United States Patent
Takruri

(10) Patent No.: US 11,090,356 B2
(45) Date of Patent: *Aug. 17, 2021

(54) AQUEOUS SUSPENSIONS OF CYCLOSPORIN

(71) Applicant: NEWPORT RESEARCH, INC., Newport Beach, CA (US)

(72) Inventor: Harun Takruri, Newport Beach, CA (US)

(73) Assignee: NEWPORT RESEARCH, INC., Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/153,736

(22) Filed: Jan. 20, 2021

(65) Prior Publication Data

US 2021/0138027 A1 May 13, 2021

Related U.S. Application Data

(63) Continuation of application No. 16/750,694, filed on Jan. 23, 2020, and a continuation-in-part of application No. 14/597,948, filed on Jan. 15, 2015, now abandoned.

(60) Provisional application No. 62/797,584, filed on Jan. 28, 2019, provisional application No. 62/797,080, filed on Jan. 25, 2019.

(51) Int. Cl.

| | | |
|---|---|---|
| *A61K 38/13* | (2006.01) | |
| *A61K 47/10* | (2017.01) | |
| *A61K 47/36* | (2006.01) | |
| *A61K 47/38* | (2006.01) | |
| *A61K 47/12* | (2006.01) | |
| *A61K 47/26* | (2006.01) | |
| *A61K 47/02* | (2006.01) | |
| *A61K 47/18* | (2017.01) | |
| *A61K 47/32* | (2006.01) | |

(52) U.S. Cl.
CPC .............. *A61K 38/13* (2013.01); *A61K 47/02* (2013.01); *A61K 47/10* (2013.01); *A61K 47/12* (2013.01); *A61K 47/186* (2013.01); *A61K 47/26* (2013.01); *A61K 47/32* (2013.01); *A61K 47/36* (2013.01); *A61K 47/38* (2013.01)

(58) Field of Classification Search
CPC ........ A61K 38/13; A61K 47/10; A61K 47/36; A61K 47/38; A61K 47/12; A61K 47/26; A61K 47/02; A61K 47/186; A61K 47/32; A61K 9/08; A61K 9/0019; A61K 9/0048
See application file for complete search history.

(56) References Cited

U.S. PATENT DOCUMENTS

| | | |
|---|---|---|
| 5,474,979 A | 12/1995 | Ding et al. |
| 5,827,822 A | 10/1998 | Floc'h et al. |
| 6,008,192 A * | 12/1999 | Al-Razzak ............... A61P 31/12 514/20.5 |
| 6,465,016 B2 | 10/2002 | Parikh et al. |
| 6,656,460 B2 | 12/2003 | Benita et al. |
| 7,026,290 B1 | 4/2006 | Domb |
| 7,335,682 B2 | 2/2008 | Chen et al. |
| 8,298,569 B2 | 10/2012 | Philips et al. |
| 8,414,904 B2 | 4/2013 | Carli et al. |
| 8,685,930 B2 | 4/2014 | Acheampong et al. |
| 8,969,385 B2 | 3/2015 | Aberg et al. |
| 9,974,793 B2 | 5/2018 | Ottoboni et al. |
| 10,137,083 B2 | 11/2018 | Lee et al. |
| 10,154,959 B1 | 12/2018 | Steele |
| 10,154,994 B2 | 12/2018 | Nguyen et al. |
| 10,918,694 B2 | 2/2021 | Weiss et al. |
| 2002/0013271 A1 | 1/2002 | Parikh et al. |
| 2003/0185892 A1 | 10/2003 | Bell et al. |
| 2004/0115287 A1 | 6/2004 | Chen et al. |
| 2004/0267214 A1 | 12/2004 | Kerssies |
| 2005/0059583 A1 | 3/2005 | Acheampong et al. |
| 2006/0148686 A1 | 7/2006 | Xia et al. |
| 2006/0210622 A1 | 9/2006 | Pace et al. |
| 2008/0124389 A1 | 5/2008 | Jenkins et al. |
| 2008/0161382 A1 | 7/2008 | Desai et al. |
| 2008/0299206 A1 | 12/2008 | Lee et al. |
| 2009/0074889 A1 | 3/2009 | Amador et al. |
| 2012/0028910 A1 | 2/2012 | Combal et al. |
| 2012/0225827 A1 | 9/2012 | Warner et al. |
| 2013/0005665 A1 | 1/2013 | Gore et al. |
| 2015/0202150 A1 | 7/2015 | Mitra et al. |
| 2019/0076354 A1 | 3/2019 | Lee et al. |

(Continued)

FOREIGN PATENT DOCUMENTS

| | | |
|---|---|---|
| AU | 2016283517 B2 | 1/2019 |
| AU | 2020203052 A1 | 5/2020 |

(Continued)

OTHER PUBLICATIONS

Tam et al (Journal of Pharmaceutical Sciences, vol. 97, No. 11, Nov. 2008) (Year: 2008).*

(Continued)

*Primary Examiner* — Sudhakar Katakam
(74) *Attorney, Agent, or Firm* — Maschoff Brennan; Brent A. Johnson

(57) ABSTRACT

Compositions that are aqueous suspensions of cyclosporin and contain a cyclosporin (e.g., cyclosporin A), a pharmaceutically acceptable water soluble solvent for the cyclosporin, a dispersing agent, a suspending agent and an aqueous vehicle are disclosed. Methods of producing such compositions, as well as methods of using the compositions to treat ophthalmic disorders are also disclosed.

21 Claims, 1 Drawing Sheet

(56) References Cited

U.S. PATENT DOCUMENTS

| | | |
|---|---|---|
| 2019/0321297 A1 | 10/2019 | McDonnell et al. |
| 2020/0009217 A1 | 1/2020 | Mitra et al. |
| 2020/0197410 A1 | 6/2020 | Ostrow et al. |

FOREIGN PATENT DOCUMENTS

| | | |
|---|---|---|
| CA | 2703000 C | 8/2013 |
| CA | 2578176 C | 9/2013 |
| EP | 696452 B1 | 7/2003 |
| EP | 1214059 B1 | 5/2005 |
| EP | 3423076 A4 | 11/2019 |
| ES | 2780182 T3 | 8/2020 |
| JP | 2960867 B2 | 10/1999 |
| JP | 2002534370 A | 10/2002 |
| JP | 2008543775 A | 12/2008 |
| JP | 4740542 B2 | 8/2011 |
| JP | 5441058 B2 | 3/2014 |
| JP | 2014506935 A | 3/2014 |
| JP | 5587936 B2 | 9/2014 |
| JP | 6731039 B2 | 7/2020 |
| KR | 101319772 B1 | 10/2013 |
| KR | 101635915 B1 | 2/2016 |
| KR | 20180117661 A | 2/2016 |
| KR | 102133381 B1 | 7/2020 |
| MX | 337149 B | 2/2016 |
| NL | 1020146 C2 | 6/2003 |
| RU | 2460516 C2 | 9/2012 |
| WO | 1998040094 A1 | 9/1998 |
| WO | 2006073786 A2 | 7/2006 |
| WO | 2006110802 A1 | 10/2006 |
| WO | 2009037583 A4 | 3/2009 |
| WO | 2017142193 A1 | 8/2017 |

OTHER PUBLICATIONS

Tamilvanan et al., The potential of lipid emulsion for ocular delivery of lipophilic drugs, European Journal of Pharmaceutics and Biopharmaceutics, 58(2), 2004, 357-358, bearing an alleged date of Sep. 2004.

Zhang et al., Pharmacokinetics and tolerance study of intravitreal injection of dexamethasone-loaded nanoparticles in rabbits, International Journal of Nanomedicine, 2009(4), 175-183, bearing an alleged date of Sep. 2009.

Lallemand et al., Successfully Improving Ocular Drug Delivery Using the Cationic Nanoemulsion, Novasorb, Hindawi Publishing Corporation, 2012, 1-16, bearing an alleged date of Feb. 2012.

Hedge et al., Microemulsion: New Insights into the Ocular Drug Delivery, Hindawi Publishing Corporation, 2013, 1-11, bearing an alleged date of Jun. 2013.

Morrison et al., Advances in ophthalmic drug delivery, Future Science Ltd., 2014, 5(12), 1297-1315, bearing an alleged date of Dec. 2014.

Lallemand et al., Cyclosporine a delivery to the eye: A comprehensive review of academic and industrial efforts, European Journal of Pharmaceutics and Biopharmaceutics, 117, 14-28, bearing an alleged date of Aug. 2017.

Restasis® product information, Jun. 2013.

* cited by examiner

AQUEOUS SUSPENSIONS OF CYCLOSPORIN

CROSS-REFERENCE TO RELATED APPLICATIONS

This application is a continuation of Ser. No. 16/750,694, filed Jan. 23, 2020, which claims the benefit of U.S. Provisional Patent Application Nos. 62/797,080, filed Jan. 25, 2019, and 62/797,584, filed Jan. 28, 2019. This application is also a continuation-in-part of Ser. No. 14/597,948, filed Jan. 15, 2015. All of the priority documents listed above are incorporated by reference in their entirety.

FIELD

The present disclosure relates generally to formulations of cyclosporin (e.g., cyclosporin A), and more specifically to aqueous suspensions of cyclosporin.

BACKGROUND

The low solubility of cyclosporins in water (e.g., below 0.004% for cyclosporin A) makes it difficult to develop therapeutically active solutions of this drug, particularly for ophthalmic use. Thus, alternate formulations have been developed for systemic and topical use based on its solubility in oils and surfactants. For example, formulations incorporating cyclosporins have been prepared as oily solutions containing ethanol. However, if oily preparations containing cyclosporins are applied directly to the eyes, irritation or a clouding of visual field may result. A further drawback of formulations containing a high concentration of oils is that oils can exacerbate the symptoms of certain ocular surface diseases such as dry eye, which is treated with cyclosporin A. Therefore, these oily formulations may not be clinically acceptable. Additionally, these formulations often suffer from physical instability due to the propensity of cyclosporin A to undergo conformational change and crystallize out. The crystallization problem has been noticed in formulations containing corn oil or medium chain triglycerides. More recent formulations are emulsions, where cyclosporin A is dissolved in oil, which then is emulsified in water with the aid of surfactants and polymers.

SUMMARY

Because cyclosporin A is soluble in oil, current formulations of cyclosporin A for topical delivery to the eye use oil as a solvent. Given that the residence time of a formulation topically applied to the eye is short, due to the cyclosporin A being washed out, such a formulation poses a problem for delivery of cyclosporin A to the eye. In particular, the cyclosporin A must diffuse out of the oily solvent, in which it is soluble, and into the hydrophilic environment of the cornea, where it is less soluble, in order to contact the cornea prior to the formulation being washed out. The present compositions address this problem by providing amorphous particles of cyclosporin (e.g., cyclosporin A) in a hydrophilic solvent/anti-solvent formulation, which will increase contact of the cyclosporin with the cornea, resulting in increased levels of cyclosporin in ocular tissues as compared to formulations of cyclosporin having oil as a solvent. Accordingly, provided herein are pharmaceutical compositions in the form of suspensions of cyclosporin (e.g., cyclosporin A) suitable for use in the eye, ear, and nose, and particularly in the eye. The present compositions are not emulsions and contain no oils or fats. The compositions contain pharmaceutically acceptable solvents for cyclosporins, which do not require removal from the final product, and an anti-solvent vehicle comprising a dispersing agent, a suspending agent, and an aqueous vehicle. The compositions are compatible with antimicrobial preservatives such as benzalkonium chloride.

Some embodiments include a pharmaceutical composition comprising: cyclosporin A, a formulation aid, water, and 1) a dispersing agent or a 2) suspending agent. In some embodiments, the composition is a suspension.

Some embodiments include a method of treating an ophthalmic disorder, comprising administering a composition disclosed herein to a mammal in need thereof, wherein a therapeutic effect is observed after administering the pharmaceutical composition.

Detailed herein are compositions comprising a cyclosporin (e.g. cyclosporin A), methods of treating disorders with the cyclosporin compositions, methods of producing the cyclosporin compositions, and further uses of the cyclosporin compositions.

DETAILED DESCRIPTION

Figure 1:
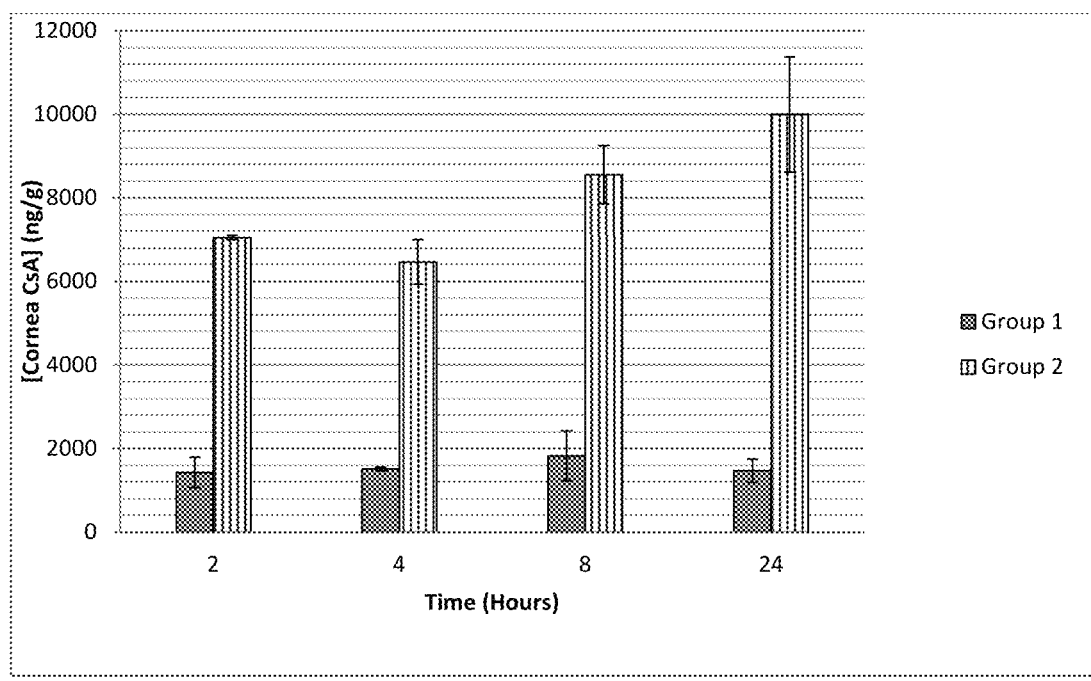
FIG. 1 is a plot of the cyclosporin A levels in cornea tissues from rabbits at the indicated time points in a study comparing a 0.05% cyclosporin A emulsion (Group 1) to a 0.05% cyclosporin A suspension of the present disclosure (Group 2).

Current formulations of cyclosporin A for topical delivery to the eye use oil as a solvent because cyclosporin A is soluble in oil, whereas it is less soluble in water. Given that the residence time of a formulation topically applied to the eye is short, due to the cyclosporin A being washed out, such a formulation poses a problem for delivery of cyclosporin A to the eye. In particular, the cyclosporin A must diffuse out of the oily solvent, in which it is soluble, and into the hydrophilic environment of the cornea, where it is less soluble, in order to contact the cornea prior to the formulation being washed out. The present compositions address this problem by providing amorphous particles of a cyclosporin (e.g., cyclosporin A) in a formulation aid/anti-solvent formulation, which will increase contact of the cyclosporin with the cornea, resulting in increased levels of cyclosporin in ocular tissues as compared to formulations of cyclosporin A having oil as a solvent. Generally, the formulation aid includes any solvent recited herein, including hydrophilic or water soluble solvents, and combination of solvents recited herein, such as combinations of hydrophilic or water soluble solvents.

The present disclosure utilizes the high solubility of cyclosporin (e.g., cyclosporin A) in organic, pharmaceutically acceptable, hydrophilic solvents to produce concentrated solutions of cyclosporin, which are then added in a small volume to aqueous anti-solvent vehicles, resulting in stable colloidal dispersions of cyclosporin suitable for use in the eye, ear, or nose. Whereas the solubility of cyclosporin A in water is about 30 µg/mL, it is about 200 mg/mL in ethanol, 400 mg/g in propylene glycol, and 260 mg/g in polyethylene glycol 400. The formulation of the present disclosure does not require removal of the organic, pharmaceutically acceptable, hydrophilic solvent from the colloidal dispersion, and rather it becomes an integral part of the formulation contributing to osmolarity and in some instances, antimicrobial properties. Thus, in some embodiments, therapeutically useful levels of 0.005 to 1.0% cyclosporin A are easily prepared while maintaining the level of the organic pharmaceutically acceptable, hydrophilic solvent in the acceptable range of tolerability.

In one aspect of the present disclosure, there are provided compositions including a cyclosporin (e.g. cyclosporin A); a formulation aid; a pharmaceutically acceptable water soluble solvent for cyclosporin; and an anti-solvent comprising a dispersing agent, a suspending agent, and an aqueous vehicle. In some embodiments, the solvent, dispersing agent, suspending agent, and aqueous vehicle are each oil-free and fat-free, and the composition is a suspension of cyclosporin and is oil-free and fat-free. In some embodiments, the suspension is formed by admixing the cyclosporin and solvent with the anti-solvent vehicle. In some embodiments, the cyclosporin is cyclosporin A. In some embodiments, the cyclosporin particles in the suspension are amorphous particles. In some embodiments, the cyclosporin is in a therapeutically effective amount. In some embodiments, the cyclosporin is in an amount between about 0.005 to 1.0% w/v. In some embodiments, the cyclosporin is cyclosporin A and is in an amount between about 0.005 to 1.0% w/v. In some embodiments, the concentration of the pharmaceutically acceptable water soluble solvent for cyclosporin is about 0.05% to about 10.0% (w/v). In some embodiments, the concentration of the pharmaceutically acceptable water soluble solvent for cyclosporin is about 0.1% to about 2.5% (w/v). In some embodiments, the concentration of the pharmaceutically acceptable water soluble solvent for cyclosporin is about 0.1% to about 5.0% (w/v). In some embodiments, the pharmaceutically acceptable water soluble solvent for cyclosporin is a solvent in which cyclosporin is highly soluble. In some embodiments, the pharmaceutically acceptable water soluble solvent for cyclosporin is a solvent having a cyclosporin solubility of at least 10 mg cyclosporin per mL of solvent. In some embodiments, the pharmaceutically acceptable water soluble solvent for cyclosporin is selected from the group consisting of ethanol, propylene glycol, polyethylene glycol (such as polyethylene glycol 300 or polyethylene glycol 3350), glycerin, benzyl alcohol, polysorbates, tyloxapol, poloxamers, acetone, DMSO, and a hydrophilic surfactant that is solid at room temperature and acts as a solvent when melted at a higher temperature. In some embodiments, the hydrophilic surfactant that is solid at room temperature is polyoxyl 15 hydroxystearate. In some embodiments, the dispersing agent is a surfactant. In some embodiments, the surfactant is selected from the group consisting of polysorbate 80, polysorbate 60, polysorbate 40, polysorbate 20, polyoxyl 40 stearate, polyoxyl 15 hydroxystearate, poloxamers, tyloxapol, POE 35 castor oil, and other pharmaceutically acceptable hydrophilic surfactants. In some embodiments, the pharmaceutically acceptable hydrophilic surfactant is an anionic surfactant or a cationic surfactant. In some embodiments, the suspending agent is selected from the group consisting of synthetic polymers, semi-synthetic polymers, and natural polymers. In some embodiments, the suspending agent is selected from the group consisting of carbomer homopolymers, carbomer copolymers, carbomer interpolymers, polycarbophil, soluble cellulose derivatives, polyvinyl alcohol, povidone (such as povidone K-90), hyaluronic acid and its salts (such as sodium hyaluronate), chondroitin sulfate, gellan, acacia, and other natural gums. In some embodiments, the suspending agent is a carbomer homopolymer (such as carbomer homopolymer type B). In some embodiments, the suspending agent is a carbomer copolymer. In some embodiments, the soluble cellulose derivative is selected from the group consisting of carboxymethylcellulose sodium (NaCMC), hydroxyethylcellulose, and hypromellose. In some embodiments, the aqueous vehicle is selected from the group consisting of water, saline, and phosphate buffered saline. In some embodiments, the composition further comprises one or more excipients. In some embodiments, the one or more excipients are selected from the group consisting of glycerin, mannitol, sorbitol, sodium chloride, tonicity adjusters, buffers, pH adjusters, chelating agents, and antioxidants. In some embodiments, the composition further comprises a preservative. In some embodiments, the preservative is selected from the group consisting of benzalkonium chloride, cetrimide, chlorobutanol, sorbic acid, and boric acid. In some embodiments, the cyclosporin is in particles of 5 μm or less. In some embodiments, the cyclosporin is in particles of 1 μm or less. In some embodiments, the composition is suitable for use in the eye. In some embodiments, the composition does not comprise a phospholipid.

In another aspect, there are provided methods of treating an ophthalmic disorder by contacting an affected eye of a patient having the ophthalmic disorder with the cyclosporin (e.g., cyclosporin A) compositions described herein, wherein the disorder is selected from the group consisting of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, vernal conjunctivitis, keratoplasty, immunoreactive graft rejection post corneal transplantation, Behcet disease, Mooren's ulcer, ocular pemphigus, and rheumatoid ulcer. In some embodiments, the ophthalmic disorder is dry eye.

In yet another aspect, there are provided methods of producing a suspension of a cyclosporin (e.g. cyclosporin A) by mixing (a) a solution of a cyclosporin dissolved in a pharmaceutically acceptable water soluble solvent for cyclosporin, and (b) an anti-solvent vehicle comprising a dispersing agent, a suspending agent, and an aqueous vehicle, thereby producing a suspension that has cyclosporin particles of 20 μm or less dispersed in the aqueous vehicle. In some embodiments, the cyclosporin is cyclosporin A. In some embodiments, the cyclosporin particles in the suspension are amorphous particles. In some embodiments, the cyclosporin is in a therapeutically effective amount. In some embodiments, the cyclosporin is in an amount between about 0.005 to 1.0% w/v. In some embodiments, the cyclosporin is cyclosporin A and is in an amount between about 0.005 to 1.0% w/v. In some embodiments, the concentration of the pharmaceutically acceptable water soluble solvent for cyclosporin is about 0.05% to about 10.0% (w/v). In some embodiments, the concentration of the pharmaceutically acceptable water soluble solvent for cyclosporin is about 0.1% to about 2.5% (w/v). In some embodiments, the concentration of the pharmaceutically acceptable water soluble solvent for cyclosporin is about 0.1% to about 5.0% (w/v). In some embodiments, the pharmaceutically acceptable water soluble solvent for cyclosporin is a solvent in which cyclosporin is highly soluble. In some embodiments, the pharmaceutically acceptable water soluble solvent for cyclosporin is a solvent having a cyclosporin solubility of at least 10 mg cyclosporin per mL of solvent. In some embodiments, the pharmaceutically acceptable water soluble solvent for cyclosporin is selected from the group consisting of ethanol, propylene glycol, polyethylene glycol (such as polyethylene glycol 300 or polyethylene glycol 3350), glycerin, benzyl alcohol, polysorbates, tyloxapol, poloxamers, acetone, DMSO, and a hydrophilic surfactant that is solid at room temperature and acts as a solvent when melted at a higher temperature. In some embodiments, the hydrophilic surfactant that is solid at room temperature is polyoxyl 15 hydroxystearate. In some embodiments, the dispersing agent is a surfactant. In some embodiments, the surfactant is selected from the group consisting of polysorbate 80, polysorbate 60, polysorbate 40, polysorbate 20, polyoxyl 40 stearate, polyoxyl 15 hydroxystearate, poloxamers, tyloxapol, POE 35 castor oil, and other pharmaceutically acceptable hydrophilic surfactants. In some embodiments, the pharmaceutically acceptable hydrophilic surfactant is an anionic surfactant or a cationic surfactant. In some embodiments, the suspending agent is selected from the group consisting of synthetic polymers, semi-synthetic polymers, and natural polymers. In some embodiments, the suspending agent is selected from the group consisting of carbomer homopolymers, carbomer copolymers, carbomer interpolymers, polycarbophil, soluble cellulose derivatives, polyvinyl alcohol, povidone (such as povidone K-90), hyaluronic acid and its salts (such as sodium hyaluronate), chondroitin sulfate, gellan, acacia, and other natural gums. In some embodiments, the suspending agent is a carbomer homopolymer (such as carbomer homopolymer type B). In some embodiments, the suspending agent is a carbomer copolymer. In some embodiments, the soluble cellulose derivative is selected from the group consisting of carboxymethylcellulose sodium (NaCMC), hydroxyethylcellulose, and hypromellose. In some embodiments, the aqueous vehicle is selected from the group consisting of water, saline, and phosphate buffered saline. In some embodiments, the composition further comprises one or more excipients. In some embodiments, the one or more excipients are selected from the group consisting of glycerin, mannitol, sorbitol, sodium chloride, tonicity adjusters, buffers, pH adjusters, chelating agents, and antioxidants. In some embodiments, the composition further comprises a preservative. In some embodiments, the preservative is selected from the group consisting of benzalkonium chloride, cetrimide, chlorobutanol, sorbic acid, and boric acid. In some embodiments, the cyclosporin is in particles of 5 µm or less. In some embodiments, the cyclosporin is in particles of 1 µm or less. In some embodiments, the composition is suitable for use in the eye. In some embodiments, the suspension does not comprise a phospholipid.

In another aspect, there are provided uses of compositions including a cyclosporin (e.g. cyclosporin A); a pharmaceutically acceptable water soluble solvent for cyclosporin; and an anti-solvent vehicle comprising a dispersing agent, a suspending agent, and an aqueous vehicle, for treating an ophthalmic disorder, wherein the disorder is selected from the group consisting of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, vernal conjunctivitis, keratoplasty, immunoreactive graft rejection post corneal transplantation, Behcet disease, Mooren's ulcer, ocular pemphigus, and rheumatoid ulcer. In some embodiments, the disorder is dry eye syndrome. In some embodiments, the suspension is formed by admixing the cyclosporin and solvent with the anti-solvent vehicle. In some embodiments, the cyclosporin is cyclosporin A. In some embodiments, the cyclosporin A particles in the suspension are amorphous particles. In some embodiments, the cyclosporin is in a therapeutically effective amount. In some embodiments, the cyclosporin is in an amount between about 0.005 to 1.0% w/v. In some embodiments, the cyclosporin is cyclosporin A and is in an amount between about 0.005 to 1.0% w/v. In some embodiments, the concentration of the pharmaceutically acceptable water soluble solvent for cyclosporin is about 0.05% to about 10.0% (w/v). In some embodiments, the concentration of the pharmaceutically acceptable water soluble solvent for cyclosporin A is about 0.1% to about 2.5% (w/v). In some embodiments, the concentration of the pharmaceutically acceptable water soluble solvent for cyclosporin is about 0.1% to about 5.0% (w/v). In some embodiments, the pharmaceutically acceptable water soluble solvent for cyclosporin is a solvent in which cyclosporin is highly soluble. In some embodiments, the pharmaceutically acceptable water soluble solvent for cyclosporin is a solvent having a cyclosporin solubility of at least 10 mg cyclosporin per mL of solvent. In some embodiments, the pharmaceutically acceptable water soluble solvent for cyclosporin is selected from the group consisting of ethanol, propylene glycol, polyethylene glycol (such as polyethylene glycol 300 or polyethylene glycol 3350), glycerin, benzyl alcohol, polysorbates, tyloxapol, poloxamers, acetone, DMSO, and a hydrophilic surfactant that is solid at room temperature and acts as a solvent when melted at a higher temperature. In some embodiments, the hydrophilic surfactant that is solid at room temperature is polyoxyl 15 hydroxystearate. In some embodiments, the dispersing agent is a surfactant. In some embodiments, the surfactant is selected from the group consisting of polysorbate 80, polysorbate 60, polysorbate 40, polysorbate 20, polyoxyl 40 stearate, polyoxyl 15 hydroxystearate, poloxamers, tyloxapol, POE 35 castor oil, and other pharmaceutically acceptable hydrophilic surfactants. In some embodiments, the pharmaceutically acceptable hydrophilic surfactant is an anionic surfactant or a cationic surfactant. In some embodiments, the suspending agent is selected from the group consisting of synthetic polymers, semi-synthetic polymers, and natural polymers. In some embodiments, the suspending agent is selected from the group consisting of carbomer homopolymers, carbomer copolymers, carbomer interpolymers, polycarbophil, soluble cellulose derivatives, polyvinyl alcohol, povidone (such as povidone K-90), hyaluronic acid and its salts (such as sodium hyaluronate), chondroitin sulfate, gellan, acacia, and other natural gums. In some embodiments, the suspending agent is a carbomer homopolymer (such as carbomer homopolymer type B). In some embodiments, the suspending agent is a carbomer copolymer. In some embodiments, the soluble cellulose derivative is selected from the group consisting of carboxymethylcellulose sodium (NaCMC), hydroxyethylcellulose, and hypromellose. In some embodiments, the aqueous vehicle is selected from the group consisting of water, saline, and phosphate buffered saline. In some embodiments, the composition further comprises one or more excipients. In some embodiments, the one or more excipients are selected from the group consisting of glycerin, mannitol, sorbitol, sodium chloride, tonicity adjusters, buffers, pH adjusters, chelating agents, and antioxidants. In some embodiments, the composition further comprises a preservative. In some embodiments, the preservative is selected from the group consisting of benzalkonium chloride, cetrimide, chlorobutanol, sorbic acid, and boric acid. In some embodiments, the cyclosporin is in particles of 5 µm or less. In some embodiments, the cyclosporin is in particles of 1 µm or less. In some embodiments, the composition is suitable for use in the eye. In some embodiments, the composition does not comprise a phospholipid.

Use of a composition including a cyclosporin; a pharmaceutically acceptable water soluble solvent for cyclosporin; and an anti-solvent vehicle comprising a dispersing agent, a suspending agent, and an aqueous vehicle, wherein the solvent for cyclosporin, dispersing agent, suspending agent, and aqueous vehicle are each oil-free and fat-free, and wherein the composition is a suspension of cyclosporin and is oil-free and fat-free for the manufacture of a medicament for the treatment of an ophthalmic disorder, wherein the disorder is selected from the group consisting of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, vernal conjunctivitis, keratoplasty, immunoreactive graft rejection post corneal transplantation, Behcet disease, Mooren's ulcer, ocular pemphigus, and rheumatoid ulcer. In some embodiments, the disorder is dry eye syndrome. In some embodiments, the cyclosporin is cyclosporin A. In some embodiments, the cyclosporin A particles are amorphous particles.

A method of treating an ophthalmic disorder comprising, contacting an affected eye of a patient having the ophthalmic disorder with a composition including a cyclosporin; a pharmaceutically acceptable water soluble solvent for cyclosporin; and an anti-solvent vehicle comprising a dispersing agent, a suspending agent, and an aqueous vehicle, wherein the disorder is selected from the group consisting of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, vernal conjunctivitis, keratoplasty, immunoreactive graft rejection post corneal transplantation, Behcet disease, Mooren's ulcer, ocular pemphigus, and rheumatoid ulcer. In some embodiments, the disorder is dry eye syndrome. In some embodiments, the cyclosporin is cyclosporin A. In some embodiments, the cyclosporin A particles are amorphous particles.

Before the present compositions and methods are described, it is to be understood that this disclosure is not limited to particular compositions, methods, and experimental conditions described, as such compositions, methods, and conditions may vary. It is also to be understood that the terminology used herein is for purposes of describing particular embodiments only, and is not intended to be limiting, since the scope of the present disclosure will be limited only in the appended embodiments.

The cyclosporins comprise a large and recognized class of cyclic peptide compounds having pharmaceutical utility, for example, immunosuppressant, anti-inflammatory, and/or anti-parasitic activity and/or activity in abrogating tumor resistance to anti-neoplastic or cytostatic drug therapy. The cyclosporins include, for example, naturally occurring fungal metabolites, such as cyclosporin A, B, C, D, E, F, G and H as well as a wide variety of synthetic and semi-synthetic cyclosporins, for example, the dihydro- and iso-cyclosporins (see e.g. U.S. Pat. Nos. 4,108,985; 4,210,581 and 4,220,641), [(D)-Ser]$^8$-Ciclosporin (see U.S. Pat. No. 4,384,996), [0-acetyl, (D)-Ser]$^8$-Ciclosporin (see U.S. Pat. No. 4,764,503), [β-fluoro-(D)Ala]$^8$-Ciclosporin (see UK Patent Application 2,206,119A), [Val]$^2$-[(D)methylthio-Sar]$^3$- and [Dihydro-MeBmt]$^1$-[Val]$^2$-[(D)methylthio-Sar]$^3$-Ciclosporin [see U.S. Pat. No. 4,703,033], [0-(2-hydroxyethyl)-(D)Ser]$^8$-Ciclosporin, and [3'-deshydroxy-3'-keto-MeBmt]$^1$-[Val]$^2$-Ciclosporin and many more. The most widely investigated cyclosporin is cyclosporin A. The terms "cyclosporin A," "cyclosporine A" and "cyclosporine" are used interchangeably herein. Cyclosporin A has been shown to suppress selectively a variety of T-lymphocyte functions, including prevention of maturation and expression of sensitized T-lymphocytes in cell mediated immune responses, and is now successfully and widely used in the suppression of organ transplant rejection. Cyclosporin A has also been used systemically in the treatment of intraocular inflammatory or autoimmune diseases, such as uveitis. Accordingly, in some embodiments, the cyclosporin used in the compositions of the present disclosure is a naturally occurring cyclosporin, a synthetic cyclosporin, or a semi-synthetic cyclosporin. In particular embodiments, the cyclosporin is cyclosporin A.

As used in this specification and the appended embodiments, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20% or ±10%, or ±5%, or even ±1% from the specified value, as such variations are appropriate for the disclosed compositions or to perform the disclosed methods.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the embodiments. The phrase "consisting essentially of" limits the scope of an embodiment to the specified materials or steps and those that do not materially affect the basic and novel characteristics of the disclosure. The present disclosure contemplates embodiments of the compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods and materials are now described.

In one aspect, there are provided compositions including a cyclosporin; a pharmaceutically acceptable water soluble solvent for cyclosporin; and an anti-solvent comprising a dispersing agent, a suspending agent, and an aqueous vehicle, wherein the solvent for cyclosporin, dispersing agent, suspending agent. In particular embodiments, the cyclosporin is cyclosporin A and the pharmaceutically acceptable water soluble solvent for cyclosporin is one in which cyclosporin A is soluble.

As used herein, the terms "oil" and "fat" refer to a substance or mixture of substances that is used or can be used as a pharmaceutical excipient, and that is very slightly soluble or insoluble in water (as defined in the USP), and has no significant surface activity in aqueous systems. Oils and fats can be mineral, synthetic, animal, or plant in origin. Exemplary oils and fats include: long chain hydrocarbons, such as mineral oil and paraffin; fatty alcohols, such as cetyl alcohol; fatty acids, such as oleic and stearic acid and other saturated and unsaturated fatty acids; synthetic fatty esters such as ethyl oleate and isopropyl myristate; triglyceride esters such as olive, peanut, sesame, castor oils, and short and medium chain mono-, di-, and triglycerides; waxes, such as beeswax and spermaceti; essential oils, such as rose, fennel, anise, peppermint and lemon oils; organic silicones, such as dimethicone and simethicone; and any other substance or mixture of substances meeting the criteria above.

The above definition of oils and fats does not include phospholipids, such as lecithin, and water-insoluble, surface active agents, such as sorbitan monooleate because they do not satisfy the above definition, and which, in some embodiments, are used as dispersing agents, by virtue of their surface activity. Similarly, components such as glycerin, PEG, POE castor oil; and polyoxyl 15 hydroxystearate are water-soluble, and carbomer homo- and copolymers disperse/hydrate readily in water, and thus, are not oils or fats as defined herein.

The cyclosporing suspensions described herein may optionally be fat-free and/or oil-free. In some embodiments, the oil-free and fat-free compositions contain about 0.1% oils and/or fats. In some embodiments, oil-free and fat-free compositions contain less than about 0.1% oils and/or fats. In some embodiments, oil-free and fat-free compositions contain less than about 0.05% oils and/or fats. In some embodiments, oil-free and fat-free compositions contain less than about 0.025% oils and/or fats. In some embodiments, oil-free and fat-free compositions contain less than about 0.01% oils and/or fats.

The term "dispersion" as used herein refers to a dispersed system having at least two phases: the substance that is dispersed, known as the dispersed phase (or internal phase), and the phase in which that substance is dispersed, known as the continuous phase (or external phase or dispersion medium). As used herein, the cyclosporin (e.g., cyclosporin A) is the dispersed phase, and the solvent/anti-solvent vehicle is the dispersion medium. Suspensions and emulsions are examples of dispersions. Based on the particle size of the dispersed phase, dispersions are generally classified as molecular dispersions (i.e., solutions), colloidal dispersions, or coarse dispersions. It is commonly accepted that molecular dispersions have dispersed particles lower than 1 nm in size; colloidal dispersions have particle sizes between 1 nm and 1 µm in size; and coarse dispersions have particles greater than 1 µm in size.

The term "suspension" as used herein refers to a dispersed system in which a finely divided solid (i.e., the dispersed phase) is dispersed uniformly in a liquid dispersion medium (i.e., the continuous phase). Suspensions are further classified as course or colloidal depending on the particle size of the dispersed phase. For example, suspensions with a particle size greater than about 1 µm are classified as coarse suspensions, while those having particles that are less than 1 µm are classified as colloidal suspensions, also called "nanosuspensions." It is desired that the internal phase be dispersed uniformly in the dispersion medium and not sediment or settle during storage, however this is difficult to achieve due to the thermodynamic instability of a suspension. Settling of a suspension requires resuspension of the dispersed phase by, for example, shaking or agitation of the composition prior to application. The prevention of settling is important for preservative-free unit dose products, where shaking is not feasible due to the small size/volume. Therefore, suspending agents that increase the viscosity and prevent the particles from settling out are used in some embodiments of the disclosed compositions. Additional stability is obtained by the use of dispersing agents that prevent the primary particles from aggregation to form larger particles susceptible to settling.

The term "emulsion" as used herein refers to a dispersed system in which a finely divided liquid (i.e., the dispersed phase) is dispersed uniformly in another liquid dispersion medium (i.e., the continuous phase) using an emulsifier. For example, in an oil-in-water emulsion, the dispersed phase is an oil, and the dispersion medium is aqueous.

In particular embodiments, the compositions are ophthalmic compositions, that is, the compositions are suitable for ophthalmic use. The ophthalmic compositions are formulated as eye-drop formulations in some embodiments. In some embodiments, the ophthalmic compositions are filled in appropriate containers to facilitate administration of the composition to the eye, for example, a plastic bottle with control dropper tip. Accordingly, in another aspect there are provided ophthalmic compositions as defined above in a container appropriate for ophthalmic application of the composition, for example, appropriate for application of the ophthalmic composition to or at the surface of the eye (e.g., to the cornea or conjunctiva). In some embodiments, the ophthalmic composition is an aqueous gel. In some embodiments, such aqueous gels are formulated by increasing the concentration of suspending agent (e.g., carbomer homopolymer, such as carbomer homopolymer type B, or carbomer copolymer) to achieve a semi-solid consistency. In some embodiments, the ophthalmic aqueous gel composition is filled into an ophthalmic ointment tube.

In some embodiments of the compositions, the cyclosporin is in a therapeutically effective amount. As used herein, a "therapeutically effective amount" or an "effective amount" is an amount of a cyclosporin or a composition thereof sufficient to effect beneficial or desired clinical results including reduction or amelioration of symptoms stemming from the disorder or condition being treated. The skilled artisan can readily determine a therapeutically effective amount of a given cyclosporin for a particular indication. In some embodiments, the cyclosporin is cyclosporin A and is present in the composition in an concentration (measured in weight/volume or w/v) between about 0.005 to 1.0%, about 0.005-0.006%, about 0.006-0.007%, about 0.007-0.008%, about 0.008-0.009%, about 0.009-0.01%, about 0.01-0.02%, about 0.02-0.03%, about 0.03-0.04%, about 0.04-0.05%, about 0.05-0.06%, about 0.06-0.07%, about 0.07-0.08%, about 0.08-0.09%, about 0.09-0.1%, about 0.1-0.5%, about 0.5-0.6%, about 0.6-0.7%, about 0.7-0.8%, about 0.8-0.9%, about 0.9-1%, about 0.5-1%, about 0.005-0.1%, about 0.01-0.05%, about 0.05-0.1%, about 0.01-0.075%, or any amount bounded by any of these ranges. In some embodiments, the cyclosporin is present in the composition at concentration of about 0.05%. As used herein, 1% (w/v) is equivalent to 1 g per 100 mL.

The compositions contain a pharmaceutically acceptable solvent for cyclosporin (e.g., cyclosporin A). As used herein, these solvents refer to a solvent in which the cyclosporin (e.g., cyclosporin A) is soluble. The term "pharmaceutically acceptable," when used in reference to a solvent, anti-solvent, vehicle, or excipient, means that the solvent, anti-solvent, vehicle, or excipient must be compatible with the other ingredients of the formulation and not deleterious to the recipient thereof. Such a component is one that is suitable for use with humans or animals without undue adverse side effects. Non-limiting examples of adverse side effects include toxicity, irritation, and/or allergic response. Such pharmaceutically acceptable solvents are organic. Further, the cyclosporin (e.g., cyclosporin A) is highly soluble in these solvents in order to produce a concentrated solution of cyclosporin. This high solubility allows the formulation of a composition to have an effective amount of cyclosporin, and allows the solvent to remain in the final composition. Because of the high solubility, the organic solvent will be present in a very small amount, thus causing little or no irritation upon application of the final composition to a patient's eye. Appropriate solvents for cyclosporin (e.g., cyclosporin A) for use in the present compositions have a solubility of, at least, about 10-20 mg/mL, about 20-30 mg/mL, about 30-40 mg/mL, about 40-50 mg/mL, about 50-60 mg/mL, about 60-70 mg/mL, about 70-80 mg/mL, about 80-90 mg/mL, about 90-100 mg/mL, about 100-110 mg/mL, about 110-120 mg/mL, about 120-130 mg/mL, about 130-140 mg/mL, about 140-150 mg/mL, about 150-160 mg/mL, about 160-170 mg/mL, about 170-180 mg/mL, about 180-190 mg/mL, about 190-200 mg/mL, about 200-500 mg/mL, about 500-2000 mg/mL or any solubility bounded by any of these ranges.

In some embodiments, the cyclosporin is cyclosporin A and the pharmaceutically acceptable water soluble solvent is one in which cyclosporin A is soluble. In some embodiments, the pharmaceutically acceptable water soluble solvent for cyclosporin (e.g., cyclosporin A) is selected from the group consisting of ethanol, propylene glycol, polyethylene glycol (such as polyethylene glycol 300 or polyethylene glycol 3350), glycerin, benzyl alcohol, polysorbates, tyloxapol, poloxamers, acetone, DMSO, hydrophilic surfactants that are solid at room temperature and act as a solvent when melted at a higher temperature, and combinations thereof. In some embodiments, the pharmaceutically acceptable water soluble solvent for cyclosporin (e.g., cyclosporin A) is selected from the group consisting of ethanol, propylene glycol, polyethylene glycol (such as polyethylene glycol 300 or polyethylene glycol 3350), glycerin, benzyl alcohol, polysorbates, tyloxapol, poloxamers, hydrophilic surfactants that are solid at room temperature and act as a solvent when melted at a higher temperature, and combinations thereof. In particular embodiments, the pharmaceutically acceptable water soluble solvent for cyclosporin (e.g., cyclosporin A) is polyethylene glycol (such as polyethylene glycol 300 or polyethylene glycol 3350). In other embodiments, the pharmaceutically acceptable water soluble solvent for cyclosporin (e.g., cyclosporin A) is alcohol. In other embodiments, the pharmaceutically acceptable water soluble solvent for cyclosporin (e.g., cyclosporin A) is ethanol. In some embodiments, the hydrophilic surfactant that is solid at room temperature is polyoxyl 15 hydroxystearate.

In some embodiments, the concentration (measured in w/v) of the pharmaceutically acceptable water soluble solvent for cyclosporin (e.g., cyclosporin A) in the compositions is within the range of about 0.05-10.0%, about 0.1-5.0%, about 0.1-2.5%, about 0.05-0.06%, about 0.06-0.07%, about 0.07-0.08%, about 0.08-0.09%, about 0.09-0.1%, about 0.1-0.2%, about 0.2-0.3%, about 0.3-0.4%, about 0.4-0.5%, about 0.5-0.6%, about 0.6-0.7%, about 0.7-0.8%, about 0.8-0.9%, about 0.9-1.0%, about 1.0-1.5%, about 1.5-2.0%, about 2.0-2.5%, about 2.5-3.0%, about 3.0-3.5%, about 3.5-4.0%, about 4.0-4.5%, about 4.5-5.0%, about 5.0-6.0%, about 6.0-7.0%, about 7.0-8.0%, about 8.0-9.0%, about 9.0-10.0%, or any concentration bounded by any of these ranges.

In some embodiments, a dispersing agent is used in the formulation to disaggregate the precipitated particles upon contact with the aqueous vehicle (e.g., "Part 2" of Example 1). In some embodiments, the dispersing agent is a surfactant. In some embodiments, the surfactant is selected from the group of surface active agents that are primarily nonionic and include without limitation polysorbate 80, polysorbate 60, polysorbate 40, polysorbate 20, polyoxyl 40 stearate, polyoxyl 15 hydroxystearate, poloxamers, tyloxapol, POE 35 castor oil, and combinations thereof. It is to be appreciated that any similar pharmaceutically acceptable surface active agents is usable at levels that do not cause irritation or discomfort when applied to the eye, ear, or nose. Accordingly, in some embodiments, the surfactant is selected from the group consisting of polysorbate 80, polysorbate 60, polysorbate 40, polysorbate 20, polyoxyl 40 stearate, polyoxyl 15 hydroxystearate, poloxamers, tyloxapol, POE 35 castor oil, and other pharmaceutically acceptable hydrophilic surfactants. In particular embodiments, the pharmaceutically acceptable hydrophilic surfactant is an anionic surfactant or a cationic surfactant. In some embodiments, the anionic surfactant is sodium lauryl sulfate or docusate sodium. In other embodiments, the cationic surfactant is benzalkonium chloride.

In some embodiments, the concentration (measured in w/v) of dispersing agent in the compositions is within the range of about 0.005%-5.0%, or from about 0.01-2.0%, about 0.01%-0.5%, about 0.005-0.006%, about 0.006-0.007%, about 0.007-0.008%, about 0.008-0.009%, about 0.009-0.01%, about 0.01-0.02%, about 0.02-0.03%, about 0.03-0.04%, about 0.04-0.05%, about 0.05-0.06%, about 0.06-0.07%, about 0.07-0.08%, about 0.08-0.09%, about 0.09-0.1%, about 0.1-0.5%, about 0.5-1.0%, about 1.0-2.0%, about 2.0-3.0%, about 3.0-4.0%, about 4.0-5.0% or any concentration bounded by any of these ranges.

In some embodiments, a suspending agent is used to increase the viscosity and enhance the physical stability of the colloidal dispersion. In some embodiments, suspending agents are polymers that are synthetic, semi-synthetic, or natural, and include without limitation: carbomer homopolymers, carbomer copolymers, carbomer interpolymers, polycarbophil, soluble cellulose derivatives such as carboxymethylcellulose sodium (NaCMC), hydroxyethylcellulose, hypromellose and others; polyvinyl alcohol, povidone (such as povidone K-90), hyaluronic acid and its salts (such as sodium hyaluronate), chondroitin sulfate, gellan, acacia, and other natural gums, and other pharmaceutically acceptable polymers. Suspending agents might also provide some surfactant properties as noted above. Accordingly, in some embodiments, the suspending agent in the composition is selected from the group consisting of carbomers, soluble cellulose derivatives, polyvinyl alcohol, povidone (such as povidone K-90), hyaluronic acid and its salts (such as sodium hyaluronate), chondroitin sulfate, gellan, acacia, and other natural gums. In some embodiments, the soluble cellulose derivative is selected from the group consisting of carboxymethylcellulose sodium (NaCMC), hydroxyethylcellulose, and hypromellose. In particular embodiments, the suspending agent is a carbomer homopolymer (such as carbomer homopolymer type B). In some embodiments, the suspending agent is a carbomer copolymer.

In some embodiments, the concentration (measure in w/v) of suspending agent in the compositions is within the range of about 0.005%-5.0%, or from about 0.01-2.0%, about 0.01%-0.5%, about 0.005-0.006%, about 0.006-0.007%, about 0.007-0.008%, about 0.008-0.009%, about 0.009-0.01%, about 0.01-0.02%, about 0.02-0.03%, about 0.03-0.04%, about 0.04-0.05%, about 0.05-0.06%, about 0.06-0.07%, about 0.07-0.08%, about 0.08-0.09%, about 0.09-0.1%, about 0.1-0.5%, about 0.5-1.0%, about 1.0-2.0%, about 2.0-3.0%, about 3.0-4.0%, about 4.0-5.0% or any concentration bounded by any of these ranges. In some embodiments, the suspending agent is at a concentration sufficient to achieve a semi-solid consistency (e.g., to form an aqueous gel).

In some embodiments, the aqueous vehicle is any pharmaceutically acceptable aqueous vehicle commonly used in ophthalmic formulations. In some embodiments, the aqueous vehicle is selected from the group consisting of water, saline, and phosphate buffered saline. In particular embodiments, the aqueous vehicle is water.

The compositions may further include one or more excipients. Such excipients are pharmaceutically acceptable components. In some embodiments, the one or more excipients are selected from the group consisting of glycerin, mannitol, sorbitol, sodium chloride, tonicity adjusters, buffers, pH adjusters, chelating agents, and antioxidants. pH adjusters include pharmaceutically acceptable acids or bases. In some embodiments, the pH adjuster is sodium hydroxide. In other embodiments, the pH adjuster is hydrochloric acid. In some embodiments, the tonicity adjuster is mannitol. In some embodiments, the tonicity adjuster is sorbitol. In some embodiments the chelating agent is edetate disodium.

The compositions may further contain an effective amount of an antimicrobial preservative. In some embodiments, any suitable preservative or combination of preservatives is employed. The amounts of preservative components included in the present compositions are sufficient to be effective in preserving the compositions and can vary based on the specific preservative component employed, the specific composition involved, the specific application involved, and the like factors. In some embodiments, preservative concentrations (measured in w/v) are in the range of about 0.00001% to about 0.5% of the composition. In some embodiments, the preservative concentration is in the range of about 0.00001-0.00005%, about 0.00005-0.0001%, about 0.0001-0.0005%, about 0.0005-0.001%, about 0.001-0.005%, about 0.005-0.01%, about 0.01-0.05%, about 0.05-0.1%, about 0.1-0.2%, about 0.2-0.3%, about 0.3-0.4%, about 0.4-0.5%, or any concentration bounded by any of these ranges. In some embodiments, other concentrations of certain preservatives are employed, as the skilled artisan can readily ascertain an effective amount of preservative for a given formulation.

Examples of suitable preservatives include, without limitation, benzalkonium chloride, methyl and ethyl parabens, hexetidine, phenyl mercuric salts and the like and mixtures thereof. Thus, in some embodiments, the preservatives include quaternary ammonium salts such as benzalkonium chloride and cetrimide, chlorobutanol, sorbic acid, boric acid, methyl and ethyl parabens, hexetidine, phenyl mercuric salts and any other preservatives known to be safe and effective when used in topical products, and mixtures thereof. In particular embodiments, the preservative is benzalkonium chloride.

Other useful preservatives include antimicrobial peptides. In some embodiments, the antimicrobial peptides include, without limitation, defensins, peptides related to defensins, cecropins, peptides related to cecropins, magainins and peptides related to magainins and other amino acid polymers with antibacterial, antifungal and/or antiviral activities. Mixtures of antimicrobial peptides or mixtures of antimicrobial peptides with other preservatives are also included within the scope of the present disclosure.

The compositions and methods are independent of pH. Any pH can be selected that does not impact the chemical stability of cyclosporin A and is tolerated by the patient upon application. An appropriate pH is readily ascertained by the skilled artisan. In some embodiments, the pH is from about 4.0 to about 9.0. In some embodiments, the pH is about 5.0-8.0, about 6.0-8.0, about 4.0-4.5, about 4.5-5.0, about 5.0-5.5, about 5.5-6.0, about 6.0-6.5, about 6.5-7.0, about 7.0-7.5, about 7.5-8.0, about 8.0-8.5, about 8.5-9.0, or any pH bounded by any of these ranges.

The present compositions are suspensions of cyclosporin (e.g., cyclosporin A). In these suspensions, cyclosporin is the dispersed phase. In some embodiments, the cyclosporin is dispersed in particles of 20 μm or less. In some embodiments, the cyclosporin is dispersed in particles of 5 μm or less. In some embodiments, the cyclosporin is dispersed in particles of 1 μm or less. In some embodiments, the cyclosporin is dispersed in particles of about 1 nm to about 1 μm, about 10-500 nm, 50-300 nm, about 1-2 nm, about 2-3 nm, about 3-4 nm, about 4-5 nm, about 5-10 nm, about 10-25 nm, about 25-50 nm, about 50-75 nm, about 75-100 nm, about 100-150 nm, about 150-200 nm, about 200-250 nm, about 230-285 nm, about 250-300 nm, about 300-350 nm, about 350-400 nm, about 400-415 nm, about 400-450 nm, 450-500 nm, about 500-600 nm, about 600-700 nm, about 700-800 nm, about 800-900 nm, about 900 nm to about 1 μm, about 1-1.5 μm, 1-2 μm, about 2-2.3 μm, about 2-3 μm, about 3-4 μm, about 4-5 μm, about 5-6 μm, about 6-7 μm, about 7-8 μm, about 8-9 μm, about 9-10 μm, about 10-11 μm, about 11-12 μm, about 12-13 μm, about 13-14 μm, about 14-15 μm, about 15-16 μm, about 16-17 μm, about 17-18 μm, about 18-19 μm, about 19-20 μm, or any particle size bounded by any of these ranges. In any of the preceding embodiments, the cyclosporin is in amorphous particles. In any of the above embodiments, the particles are non-aggregating. In any of the preceding embodiments, the cyclosporin is cyclosporin A.

Table 1 includes various embodiments with potential amounts of cyclosporin A and formulation aid. Each of these embodiments also includes 0-5% (w/v) of dispersing agent and 0-5% (w/v) of suspending agent.

TABLE 1

| Embodiment | Cyclosporin A (w/v) | Formulation Aid (w/v) |
|---|---|---|
| 1-1 | 0.01-0.02% | 0.01-0.2% |
| 1-2 | 0.02-0.03% | 0.01-0.2% |
| 1-3 | 0.03-0.04% | 0.01-0.2% |
| 1-4 | 0.04-0.05% | 0.01-0.2% |
| 1-5 | 0.05-0.06% | 0.01-0.2% |
| 1-6 | 0.06-0.07% | 0.01-0.2% |
| 1-7 | 0.07-0.08% | 0.01-0.2% |
| 1-8 | 0.08-0.09% | 0.01-0.2% |
| 1-9 | 0.09-0.1% | 0.01-0.2% |
| 1-10 | 0.1-0.2% | 0.01-0.2% |
| 1-11 | 0.2-0.3% | 0.01-0.2% |
| 1-12 | 0.3-0.4% | 0.01-0.2% |
| 1-13 | 0.4-0.5% | 0.01-0.2% |
| 1-14 | 0.5-0.6% | 0.01-0.2% |
| 1-15 | 0.6-0.7% | 0.01-0.2% |
| 1-16 | 0.7-0.8% | 0.01-0.2% |
| 1-17 | 0.8-0.9% | 0.01-0.2% |
| 1-18 | 0.9-1% | 0.01-0.2% |
| 1-19 | 0.01-0.02% | 0.2-0.3% |
| 1-20 | 0.02-0.03% | 0.2-0.3% |
| 1-21 | 0.03-0.04% | 0.2-0.3% |
| 1-22 | 0.04-0.05% | 0.2-0.3% |
| 1-23 | 0.05-0.06% | 0.2-0.3% |
| 1-24 | 0.06-0.07% | 0.2-0.3% |
| 1-25 | 0.07-0.08% | 0.2-0.3% |
| 1-26 | 0.08-0.09% | 0.2-0.3% |
| 1-27 | 0.09-0.1% | 0.2-0.3% |
| 1-28 | 0.1-0.2% | 0.2-0.3% |
| 1-29 | 0.2-0.3% | 0.2-0.3% |

TABLE 1-continued

| Embodiment | Cyclosporin A (w/v) | Formulation Aid (w/v) |
|---|---|---|
| 1-30 | 0.3-0.4% | 0.2-0.3% |
| 1-31 | 0.4-0.5% | 0.2-0.3% |
| 1-32 | 0.5-0.6% | 0.2-0.3% |
| 1-33 | 0.6-0.7% | 0.2-0.3% |
| 1-34 | 0.7-0.8% | 0.2-0.3% |
| 1-35 | 0.8-0.9% | 0.2-0.3% |
| 1-36 | 0.9-1% | 0.2-0.3% |
| 1-37 | 0.01-0.02% | 0.3-0.4% |
| 1-38 | 0.02-0.03% | 0.3-0.4% |
| 1-39 | 0.03-0.04% | 0.3-0.4% |
| 1-40 | 0.04-0.05% | 0.3-0.4% |
| 1-41 | 0.05-0.06% | 0.3-0.4% |
| 1-42 | 0.06-0.07% | 0.3-0.4% |
| 1-43 | 0.07-0.08% | 0.3-0.4% |
| 1-44 | 0.08-0.09% | 0.3-0.4% |
| 1-45 | 0.09-0.1% | 0.3-0.4% |
| 1-46 | 0.1-0.2% | 0.3-0.4% |
| 1-47 | 0.2-0.3% | 0.3-0.4% |
| 1-48 | 0.3-0.4% | 0.3-0.4% |
| 1-49 | 0.4-0.5% | 0.3-0.4% |
| 1-50 | 0.5-0.6% | 0.3-0.4% |
| 1-51 | 0.6-0.7% | 0.3-0.4% |
| 1-52 | 0.7-0.8% | 0.3-0.4% |
| 1-53 | 0.8-0.9% | 0.3-0.4% |
| 1-54 | 0.9-1% | 0.3-0.4% |
| 1-55 | 0.01-0.02% | 0.4-0.5% |
| 1-56 | 0.02-0.03% | 0.4-0.5% |
| 1-57 | 0.03-0.04% | 0.4-0.5% |
| 1-58 | 0.04-0.05% | 0.4-0.5% |
| 1-59 | 0.05-0.06% | 0.4-0.5% |
| 1-60 | 0.06-0.07% | 0.4-0.5% |
| 1-61 | 0.07-0.08% | 0.4-0.5% |
| 1-62 | 0.08-0.09% | 0.4-0.5% |
| 1-63 | 0.09-0.1% | 0.4-0.5% |
| 1-64 | 0.1-0.2% | 0.4-0.5% |
| 1-65 | 0.2-0.3% | 0.4-0.5% |
| 1-66 | 0.3-0.4% | 0.4-0.5% |
| 1-67 | 0.4-0.5% | 0.4-0.5% |
| 1-68 | 0.5-0.6% | 0.4-0.5% |
| 1-69 | 0.6-0.7% | 0.4-0.5% |
| 1-70 | 0.7-0.8% | 0.4-0.5% |
| 1-71 | 0.8-0.9% | 0.4-0.5% |
| 1-72 | 0.9-1% | 0.4-0.5% |
| 1-73 | 0.01-0.02% | 0.5-0.6% |
| 1-74 | 0.02-0.03% | 0.5-0.6% |
| 1-75 | 0.03-0.04% | 0.5-0.6% |
| 1-76 | 0.04-0.05% | 0.5-0.6% |
| 1-77 | 0.05-0.06% | 0.5-0.6% |
| 1-78 | 0.06-0.07% | 0.5-0.6% |
| 1-79 | 0.07-0.08% | 0.5-0.6% |
| 1-80 | 0.08-0.09% | 0.5-0.6% |
| 1-81 | 0.09-0.1% | 0.5-0.6% |
| 1-82 | 0.1-0.2% | 0.5-0.6% |
| 1-83 | 0.2-0.3% | 0.5-0.6% |
| 1-84 | 0.3-0.4% | 0.5-0.6% |
| 1-85 | 0.4-0.5% | 0.5-0.6% |
| 1-86 | 0.5-0.6% | 0.5-0.6% |
| 1-87 | 0.6-0.7% | 0.5-0.6% |
| 1-88 | 0.7-0.8% | 0.5-0.6% |
| 1-89 | 0.8-0.9% | 0.5-0.6% |
| 1-90 | 0.9-1% | 0.5-0.6% |
| 1-91 | 0.01-0.02% | 0.6-0.7% |
| 1-92 | 0.02-0.03% | 0.6-0.7% |
| 1-93 | 0.03-0.04% | 0.6-0.7% |
| 1-94 | 0.04-0.05% | 0.6-0.7% |
| 1-95 | 0.05-0.06% | 0.6-0.7% |
| 1-96 | 0.06-0.07% | 0.6-0.7% |
| 1-97 | 0.07-0.08% | 0.6-0.7% |
| 1-98 | 0.08-0.09% | 0.6-0.7% |
| 1-99 | 0.09-0.1% | 0.6-0.7% |
| 1-100 | 0.1-0.2% | 0.6-0.7% |
| 1-101 | 0.2-0.3% | 0.6-0.7% |
| 1-102 | 0.3-0.4% | 0.6-0.7% |
| 1-103 | 0.4-0.5% | 0.6-0.7% |
| 1-104 | 0.5-0.6% | 0.6-0.7% |
| 1-105 | 0.6-0.7% | 0.6-0.7% |
| 1-106 | 0.7-0.8% | 0.6-0.7% |
| 1-107 | 0.8-0.9% | 0.6-0.7% |
| 1-108 | 0.9-1% | 0.6-0.7% |
| 1-109 | 0.01-0.02% | 0.7-0.8% |
| 1-110 | 0.02-0.03% | 0.7-0.8% |
| 1-111 | 0.03-0.04% | 0.7-0.8% |
| 1-112 | 0.04-0.05% | 0.7-0.8% |
| 1-113 | 0.05-0.06% | 0.7-0.8% |
| 1-114 | 0.06-0.07% | 0.7-0.8% |
| 1-115 | 0.07-0.08% | 0.7-0.8% |
| 1-116 | 0.08-0.09% | 0.7-0.8% |
| 1-117 | 0.09-0.1% | 0.7-0.8% |
| 1-118 | 0.1-0.2% | 0.7-0.8% |
| 1-119 | 0.2-0.3% | 0.7-0.8% |
| 1-120 | 0.3-0.4% | 0.7-0.8% |
| 1-121 | 0.4-0.5% | 0.7-0.8% |
| 1-122 | 0.5-0.6% | 0.7-0.8% |
| 1-123 | 0.6-0.7% | 0.7-0.8% |
| 1-124 | 0.7-0.8% | 0.7-0.8% |
| 1-125 | 0.8-0.9% | 0.7-0.8% |
| 1-126 | 0.9-1% | 0.7-0.8% |
| 1-127 | 0.01-0.02% | 0.8-0.9% |
| 1-128 | 0.02-0.03% | 0.8-0.9% |
| 1-129 | 0.03-0.04% | 0.8-0.9% |
| 1-130 | 0.04-0.05% | 0.8-0.9% |
| 1-131 | 0.05-0.06% | 0.8-0.9% |
| 1-132 | 0.06-0.07% | 0.8-0.9% |
| 1-133 | 0.07-0.08% | 0.8-0.9% |
| 1-134 | 0.08-0.09% | 0.8-0.9% |
| 1-135 | 0.09-0.1% | 0.8-0.9% |
| 1-136 | 0.1-0.2% | 0.8-0.9% |
| 1-137 | 0.2-0.3% | 0.8-0.9% |
| 1-138 | 0.3-0.4% | 0.8-0.9% |
| 1-139 | 0.4-0.5% | 0.8-0.9% |
| 1-140 | 0.5-0.6% | 0.8-0.9% |
| 1-141 | 0.6-0.7% | 0.8-0.9% |
| 1-142 | 0.7-0.8% | 0.8-0.9% |
| 1-143 | 0.8-0.9% | 0.8-0.9% |
| 1-144 | 0.9-1% | 0.8-0.9% |
| 1-145 | 0.01-0.02% | 0.9-1% |
| 1-146 | 0.02-0.03% | 0.9-1% |
| 1-147 | 0.03-0.04% | 0.9-1% |
| 1-148 | 0.04-0.05% | 0.9-1% |
| 1-149 | 0.05-0.06% | 0.9-1% |
| 1-150 | 0.06-0.07% | 0.9-1% |
| 1-151 | 0.07-0.08% | 0.9-1% |
| 1-152 | 0.08-0.09% | 0.9-1% |
| 1-153 | 0.09-0.1% | 0.9-1% |
| 1-154 | 0.1-0.2% | 0.9-1% |
| 1-155 | 0.2-0.3% | 0.9-1% |
| 1-156 | 0.3-0.4% | 0.9-1% |
| 1-157 | 0.4-0.5% | 0.9-1% |
| 1-158 | 0.5-0.6% | 0.9-1% |
| 1-159 | 0.6-0.7% | 0.9-1% |
| 1-160 | 0.7-0.8% | 0.9-1% |
| 1-161 | 0.8-0.9% | 0.9-1% |
| 1-162 | 0.9-1% | 0.9-1% |
| 1-163 | 0.01-0.02% | 1-2% |
| 1-164 | 0.02-0.03% | 1-2% |
| 1-165 | 0.03-0.04% | 1-2% |
| 1-166 | 0.04-0.05% | 1-2% |
| 1-167 | 0.05-0.06% | 1-2% |
| 1-168 | 0.06-0.07% | 1-2% |
| 1-169 | 0.07-0.08% | 1-2% |
| 1-170 | 0.08-0.09% | 1-2% |
| 1-171 | 0.09-0.1% | 1-2% |
| 1-172 | 0.1-0.2% | 1-2% |
| 1-173 | 0.2-0.3% | 1-2% |
| 1-174 | 0.3-0.4% | 1-2% |
| 1-175 | 0.4-0.5% | 1-2% |
| 1-176 | 0.5-0.6% | 1-2% |
| 1-177 | 0.6-0.7% | 1-2% |
| 1-178 | 0.7-0.8% | 1-2% |
| 1-179 | 0.8-0.9% | 1-2% |
| 1-180 | 0.9-1% | 1-2% |
| 1-181 | 0.01-0.02% | 2-3% |
| 1-182 | 0.02-0.03% | 2-3% |
| 1-183 | 0.03-0.04% | 2-3% |

TABLE 1-continued

| Embodiment | Cyclosporin A (w/v) | Formulation Aid (w/v) |
|---|---|---|
| 1-184 | 0.04-0.05% | 2-3% |
| 1-185 | 0.05-0.06% | 2-3% |
| 1-186 | 0.06-0.07% | 2-3% |
| 1-187 | 0.07-0.08% | 2-3% |
| 1-188 | 0.08-0.09% | 2-3% |
| 1-189 | 0.09-0.1% | 2-3% |
| 1-190 | 0.1-0.2% | 2-3% |
| 1-191 | 0.2-0.3% | 2-3% |
| 1-192 | 0.3-0.4% | 2-3% |
| 1-193 | 0.4-0.5% | 2-3% |
| 1-194 | 0.5-0.6% | 2-3% |
| 1-195 | 0.6-0.7% | 2-3% |
| 1-196 | 0.7-0.8% | 2-3% |
| 1-197 | 0.8-0.9% | 2-3% |
| 1-198 | 0.9-1% | 2-3% |
| 1-199 | 0.01-0.02% | 3-4% |
| 1-200 | 0.02-0.03% | 3-4% |
| 1-201 | 0.03-0.04% | 3-4% |
| 1-202 | 0.04-0.05% | 3-4% |
| 1-203 | 0.05-0.06% | 3-4% |
| 1-204 | 0.06-0.07% | 3-4% |
| 1-205 | 0.07-0.08% | 3-4% |
| 1-206 | 0.08-0.09% | 3-4% |
| 1-207 | 0.09-0.1% | 3-4% |
| 1-208 | 0.1-0.2% | 3-4% |
| 1-209 | 0.2-0.3% | 3-4% |
| 1-210 | 0.3-0.4% | 3-4% |
| 1-211 | 0.4-0.5% | 3-4% |
| 1-212 | 0.5-0.6% | 3-4% |
| 1-213 | 0.6-0.7% | 3-4% |
| 1-214 | 0.7-0.8% | 3-4% |
| 1-215 | 0.8-0.9% | 3-4% |
| 1-216 | 0.9-1% | 3-4% |
| 1-217 | 0.01-0.02% | 4-5% |
| 1-218 | 0.02-0.03% | 4-5% |
| 1-219 | 0.03-0.04% | 4-5% |
| 1-220 | 0.04-0.05% | 4-5% |
| 1-221 | 0.05-0.06% | 4-5% |
| 1-222 | 0.06-0.07% | 4-5% |
| 1-223 | 0.07-0.08% | 4-5% |
| 1-224 | 0.08-0.09% | 4-5% |
| 1-225 | 0.09-0.1% | 4-5% |
| 1-226 | 0.1-0.2% | 4-5% |
| 1-227 | 0.2-0.3% | 4-5% |
| 1-228 | 0.3-0.4% | 4-5% |
| 1-229 | 0.4-0.5% | 4-5% |
| 1-230 | 0.5-0.6% | 4-5% |
| 1-231 | 0.6-0.7% | 4-5% |
| 1-232 | 0.7-0.8% | 4-5% |
| 1-233 | 0.8-0.9% | 4-5% |
| 1-234 | 0.9-1% | 4-5% |
| 1-235 | 0.01-0.02% | 5-6% |
| 1-236 | 0.02-0.03% | 5-6% |
| 1-237 | 0.03-0.04% | 5-6% |
| 1-238 | 0.04-0.05% | 5-6% |
| 1-239 | 0.05-0.06% | 5-6% |
| 1-240 | 0.06-0.07% | 5-6% |
| 1-241 | 0.07-0.08% | 5-6% |
| 1-242 | 0.08-0.09% | 5-6% |
| 1-243 | 0.09-0.1% | 5-6% |
| 1-244 | 0.1-0.2% | 5-6% |
| 1-245 | 0.2-0.3% | 5-6% |
| 1-246 | 0.3-0.4% | 5-6% |
| 1-247 | 0.4-0.5% | 5-6% |
| 1-248 | 0.5-0.6% | 5-6% |
| 1-249 | 0.6-0.7% | 5-6% |
| 1-250 | 0.7-0.8% | 5-6% |
| 1-251 | 0.8-0.9% | 5-6% |
| 1-252 | 0.9-1% | 5-6% |
| 1-253 | 0.01-0.02% | 6-7% |
| 1-254 | 0.02-0.03% | 6-7% |
| 1-255 | 0.03-0.04% | 6-7% |
| 1-256 | 0.04-0.05% | 6-7% |
| 1-257 | 0.05-0.06% | 6-7% |
| 1-258 | 0.06-0.07% | 6-7% |
| 1-259 | 0.07-0.08% | 6-7% |
| 1-260 | 0.08-0.09% | 6-7% |
| 1-261 | 0.09-0.1% | 6-7% |
| 1-262 | 0.1-0.2% | 6-7% |
| 1-263 | 0.2-0.3% | 6-7% |
| 1-264 | 0.3-0.4% | 6-7% |
| 1-265 | 0.4-0.5% | 6-7% |
| 1-266 | 0.5-0.6% | 6-7% |
| 1-267 | 0.6-0.7% | 6-7% |
| 1-268 | 0.7-0.8% | 6-7% |
| 1-269 | 0.8-0.9% | 6-7% |
| 1-270 | 0.9-1% | 6-7% |
| 1-271 | 0.01-0.02% | 7-8% |
| 1-272 | 0.02-0.03% | 7-8% |
| 1-273 | 0.03-0.04% | 7-8% |
| 1-274 | 0.04-0.05% | 7-8% |
| 1-275 | 0.05-0.06% | 7-8% |
| 1-276 | 0.06-0.07% | 7-8% |
| 1-277 | 0.07-0.08% | 7-8% |
| 1-278 | 0.08-0.09% | 7-8% |
| 1-279 | 0.09-0.1% | 7-8% |
| 1-280 | 0.1-0.2% | 7-8% |
| 1-281 | 0.2-0.3% | 7-8% |
| 1-282 | 0.3-0.4% | 7-8% |
| 1-283 | 0.4-0.5% | 7-8% |
| 1-284 | 0.5-0.6% | 7-8% |
| 1-285 | 0.6-0.7% | 7-8% |
| 1-286 | 0.7-0.8% | 7-8% |
| 1-287 | 0.8-0.9% | 7-8% |
| 1-288 | 0.9-1% | 7-8% |
| 1-289 | 0.01-0.02% | 8-9% |
| 1-290 | 0.02-0.03% | 8-9% |
| 1-291 | 0.03-0.04% | 8-9% |
| 1-292 | 0.04-0.05% | 8-9% |
| 1-293 | 0.05-0.06% | 8-9% |
| 1-294 | 0.06-0.07% | 8-9% |
| 1-295 | 0.07-0.08% | 8-9% |
| 1-296 | 0.08-0.09% | 8-9% |
| 1-297 | 0.09-0.1% | 8-9% |
| 1-298 | 0.1-0.2% | 8-9% |
| 1-299 | 0.2-0.3% | 8-9% |
| 1-300 | 0.3-0.4% | 8-9% |
| 1-301 | 0.4-0.5% | 8-9% |
| 1-302 | 0.5-0.6% | 8-9% |
| 1-303 | 0.6-0.7% | 8-9% |
| 1-304 | 0.7-0.8% | 8-9% |
| 1-305 | 0.8-0.9% | 8-9% |
| 1-306 | 0.9-1% | 8-9% |
| 1-307 | 0.01-0.02% | 9-10% |
| 1-308 | 0.02-0.03% | 9-10% |
| 1-309 | 0.03-0.04% | 9-10% |
| 1-310 | 0.04-0.05% | 9-10% |
| 1-311 | 0.05-0.06% | 9-10% |
| 1-312 | 0.06-0.07% | 9-10% |
| 1-313 | 0.07-0.08% | 9-10% |
| 1-314 | 0.08-0.09% | 9-10% |
| 1-315 | 0.09-0.1% | 9-10% |
| 1-316 | 0.1-0.2% | 9-10% |
| 1-317 | 0.2-0.3% | 9-10% |
| 1-318 | 0.3-0.4% | 9-10% |
| 1-319 | 0.4-0.5% | 9-10% |
| 1-320 | 0.5-0.6% | 9-10% |
| 1-321 | 0.6-0.7% | 9-10% |
| 1-322 | 0.7-0.8% | 9-10% |
| 1-323 | 0.8-0.9% | 9-10% |
| 1-324 | 0.9-1% | 9-10% |
| 1-325 | 0.01-0.02% | 0.01-0.5% |
| 1-326 | 0.02-0.03% | 0.01-0.5% |
| 1-327 | 0.03-0.04% | 0.01-0.5% |
| 1-328 | 0.04-0.05% | 0.01-0.5% |
| 1-329 | 0.05-0.06% | 0.01-0.5% |
| 1-330 | 0.06-0.07% | 0.01-0.5% |
| 1-331 | 0.07-0.08% | 0.01-0.5% |
| 1-332 | 0.08-0.09% | 0.01-0.5% |
| 1-333 | 0.09-0.1% | 0.01-0.5% |
| 1-334 | 0.1-0.2% | 0.01-0.5% |
| 1-335 | 0.2-0.3% | 0.01-0.5% |
| 1-336 | 0.3-0.4% | 0.01-0.5% |
| 1-337 | 0.4-0.5% | 0.01-0.5% |

TABLE 1-continued

| Embodiment | Cyclosporin A (w/v) | Formulation Aid (w/v) |
|---|---|---|
| 1-338 | 0.5-0.6% | 0.01-0.5% |
| 1-339 | 0.6-0.7% | 0.01-0.5% |
| 1-340 | 0.7-0.8% | 0.01-0.5% |
| 1-341 | 0.8-0.9% | 0.01-0.5% |
| 1-342 | 0.9-1% | 0.01-0.5% |
| 1-343 | 0.01-0.02% | 0.5-1% |
| 1-344 | 0.02-0.03% | 0.5-1% |
| 1-345 | 0.03-0.04% | 0.5-1% |
| 1-346 | 0.04-0.05% | 0.5-1% |
| 1-347 | 0.05-0.06% | 0.5-1% |
| 1-348 | 0.06-0.07% | 0.5-1% |
| 1-349 | 0.07-0.08% | 0.5-1% |
| 1-350 | 0.08-0.09% | 0.5-1% |
| 1-351 | 0.09-0.1% | 0.5-1% |
| 1-352 | 0.1-0.2% | 0.5-1% |
| 1-353 | 0.2-0.3% | 0.5-1% |
| 1-354 | 0.3-0.4% | 0.5-1% |
| 1-355 | 0.4-0.5% | 0.5-1% |
| 1-356 | 0.5-0.6% | 0.5-1% |
| 1-357 | 0.6-0.7% | 0.5-1% |
| 1-358 | 0.7-0.8% | 0.5-1% |
| 1-359 | 0.8-0.9% | 0.5-1% |
| 1-360 | 0.9-1% | 0.5-1% |
| 1-361 | 0.01-0.02% | 1-5% |
| 1-362 | 0.02-0.03% | 1-5% |
| 1-363 | 0.03-0.04% | 1-5% |
| 1-364 | 0.04-0.05% | 1-5% |
| 1-365 | 0.05-0.06% | 1-5% |
| 1-366 | 0.06-0.07% | 1-5% |
| 1-367 | 0.07-0.08% | 1-5% |
| 1-368 | 0.08-0.09% | 1-5% |
| 1-369 | 0.09-0.1% | 1-5% |
| 1-370 | 0.1-0.2% | 1-5% |
| 1-371 | 0.2-0.3% | 1-5% |
| 1-372 | 0.3-0.4% | 1-5% |
| 1-373 | 0.4-0.5% | 1-5% |
| 1-374 | 0.5-0.6% | 1-5% |
| 1-375 | 0.6-0.7% | 1-5% |
| 1-376 | 0.7-0.8% | 1-5% |
| 1-377 | 0.8-0.9% | 1-5% |
| 1-378 | 0.9-1% | 1-5% |
| 1-379 | 0.01-0.02% | 5-10% |
| 1-380 | 0.02-0.03% | 5-10% |
| 1-381 | 0.03-0.04% | 5-10% |
| 1-382 | 0.04-0.05% | 5-10% |
| 1-383 | 0.05-0.06% | 5-10% |
| 1-384 | 0.06-0.07% | 5-10% |
| 1-385 | 0.07-0.08% | 5-10% |
| 1-386 | 0.08-0.09% | 5-10% |
| 1-387 | 0.09-0.1% | 5-10% |
| 1-388 | 0.1-0.2% | 5-10% |
| 1-389 | 0.2-0.3% | 5-10% |
| 1-390 | 0.3-0.4% | 5-10% |
| 1-391 | 0.4-0.5% | 5-10% |
| 1-392 | 0.5-0.6% | 5-10% |
| 1-393 | 0.6-0.7% | 5-10% |
| 1-394 | 0.7-0.8% | 5-10% |
| 1-395 | 0.8-0.9% | 5-10% |
| 1-396 | 0.9-1% | 5-10% |

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a solvent having a cyclosporin solubility of at least 10 mg cyclosporin per mL of solvent.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a solvent having a cyclosporin solubility of at least 2 mg cyclosporin per mL of solvent.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is ethanol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is propylene glycol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is polyethylene glycol (such as polyethylene glycol 300 or polyethylene glycol 3350).

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is glycerin.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is benzyl alcohol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a polyoxyl derivative of a fatty acid.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a polyoxyl derivative of a fatty alcohol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a polysorbate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is tyloxapol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a poloxamer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is acetone.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is dimethylsulfoxide (DMSO).

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is a hydrophilic surfactant that is solid at room temperature and acts as a solvent when melted at a higher temperature.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the formulation aid is polyoxyl 15 hydroxystearate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polysorbate 80.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polysorbate 60.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polysorbate 40.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polysorbate 20.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a sorbitan.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a polyoxyl derivative of a fatty acid.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a polyoxyl derivative of a fatty alcohol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polyoxyl 40 stearate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is polyoxyl 15 hydroxystearate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a poloxamer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is tyloxapol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is POE 35 castor oil.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is an anionic surfactant.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is sodium lauryl sulfate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is docusate sodium or another docusate salt.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a cationic surfactant.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is benzalkonium chloride.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is cetrimonium bromide.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the dispersing agent is a saponin.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a hydrophilic synthetic polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a natural polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a carbomer homopolymer (such as carbomer homopolymer type B).

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a carbomer copolymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a carbomer interpolymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a polycarbophil.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a soluble cellulose derivative.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a polyvinyl alcohol.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a povidone (such as povidone K-90).

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a hyaluronic acid or a salt thereof (such as sodium hyaluronate).

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a chondroitin sulfate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a xanthan gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a gellan.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is acacia.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a natural gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a gellan gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is an agar.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is an agarose.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a carrageenan.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a guar gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a locust-bean gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a tara gum.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a carboxymethylcellulose or a salt thereof.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a hydroxyethylcellulose.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a hypromellose.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a gelatin.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is an alginate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a sodium alginate.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a pectin.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a soluble pectin.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a starch.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a soluble starch.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a starch derivative.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a chitosan.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is chitosan derivative.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a nonionic polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1- 69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a cationic polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is an anionic polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is an amphoteric polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a soluble silicone polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the suspending agent is a dimethicone copolylol polymer.

With respect to some embodiments, such as Embodiment 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63,1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, or 1-396, in some embodiments, the combination of the formulation aid, the dispersing agent, and the suspending agent is one of those specified in Table 2.

The ophthalmic compositions are useful for the same indications as other topical ophthalmic compositions containing cyclosporin (e.g., cyclosporin A), for example diseases affecting the cornea, the aqueous, the lens, the iris, the ciliary, the choroid or the retina. The ophthalmic compositions are useful particularly for the treatment of an autoimmune or inflammatory disease or condition of the eye or of the surrounding or associated organs or tissues, which has undesirably elevated immune response or inflammatory reaction or event as part of its etiology. In some embodiments, the ophthalmic compositions are used for treating the anterior or posterior segment of the eye. For example, in some embodiments, the compositions are used for the treatment of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, including vernal conjunctivitis, or in keratoplasty. The ophthalmic compositions may also be used in the treatment of immunoreactive graft rejection post corneal transplantation, Behcet disease, and autoimmune corneal diseases such as Mooren's ulcer, ocular pemphigus, and rheumatoid ulcer.

Accordingly, there are provided methods of treating an ophthalmic disorder in a patient by contacting an affected eye of a patient having the ophthalmic disorder with the disclosed cyclosporin compositions, wherein the disorder is selected from the group consisting of dry eye syndrome, anterior or posterior uveitis, chronic keratitis, keratoconjunctivitis sicca, vernal keratoconjunctivitis, phacoanaphylactic endophthalmitis, atopic keratoconjunctivitis, conjunctivitis, vernal conjunctivitis, keratoplasty, immunoreactive graft rejection post corneal transplantation, Behcet disease, Mooren's ulcer, ocular pemphigus, and rheumatoid ulcer. In some embodiments, the disorder is selected from the group consisting of dry eye syndrome, phacoanaphylactic endophthalmitis, uveitis, vernal conjunctivitis, atopic keratoconjunctivitis, and corneal graft rejection, thereby treating the disorder. In some embodiments, the disorder is dry eye. In some embodiments, the cyclosporin is cyclosporin A.

As used herein, "treatment" or "treating" is an approach for obtaining beneficial or desired clinical results. For purposes of this disclosure, beneficial or desired clinical results include, but are not limited to, reduction or amelioration of symptoms stemming from the disorder or condition being treated.

In yet another aspect, there are provided methods of producing an oil-free, fat-free cyclosporin suspension by mixing (a) a solution of a cyclosporin dissolved in a pharmaceutically acceptable water soluble solvent for the cyclosporin, and (b) an anti-solvent vehicle comprising a dispersing agent, a suspending agent, and an aqueous vehicle, wherein the solution and the anti-solvent vehicle are each oil-free and fat-free, thereby producing a suspension that is oil-free and fat-free and having cyclosporin particles of 20 μm or less dispersed in the aqueous vehicle. In particular embodiments, the cyclosporin is cyclosporin A and the pharmaceutically acceptable water soluble solvent is one in which cyclosporin A is soluble.

In general, the suspensions provided herein are prepared by adding the dispersed phase (e.g., a solution of cyclosporin dissolved in a relatively small volume of the hydrophilic solvent for the cyclosporin) to a large volume of the dispersion medium (e.g., an anti-solvent vehicle prepared by pre-mixing the suspending agent, dispersing agent, aqueous vehicle, and any other desired agents or components). In some embodiments, the dispersed phase of the suspension is prepared by dissolving the cyclosporin (e.g., cyclosporin A) in a sufficient volume of the hydrophilic solvent to solubilize the cyclosporin. For hydrophilic solvents that are solid at room temperature, these solvents are heated to a temperature sufficient to melt the solid, and then the cyclosporin is dissolved in the liquid form of the solvent. In some embodiments, a suitable temperature for preparation of a composition is determined by routine experimentation. Where the hydrophilic solvent is a liquid at room temperature, no heating is necessary. The dispersion medium is prepared by dissolving the suspending agent, the dispersing agent, and any other optional components such as preservatives or excipients into an appropriate volume of aqueous vehicle.

Methods of mixing the phases are well-known in the art and can employ a mixer such as an OMNI stator-rotor mixer or equivalent. In some embodiments, the size of the cyclosporin particles produced depends on the batch processing temperature.

In some embodiments, the compositions of the present disclosure are sterilized by preparing two sterile parts and combining them aseptically. For example, in some embodiments, the first part (Part 1) is the solution of cyclosporin A in the designated solvent(s) and is sterilized by filtration using, for example, a 0.22 micron filter; and the second part (Part 2) consists of the remaining components and is sterilized using heat (e.g., autoclave steam sterilization) or, if the viscosity is low enough, sterile filtration using 0.22 micron filters. This procedure minimizes exposure of cyclosporin A to potential degradation by heat. However, in certain embodiments the complete formulation is sterilizable by autoclaving without undue effect on the stability of cyclosporin A.

The following examples are intended to illustrate but not limit the scope of the disclosure. In these examples "Carbomer Homopolymer Type B" refers to CARBOPOL 974P NF carbomer homopolymer type B (manufactured by Lubrizol).

EXAMPLES

Example 1

| Ingredient | % w/v |
| --- | --- |
| Cyclosporin A | 0.10 |
| Polyethylene Glycol 300 | 2.0 |
| Carbomer Homopolymer Type B | 0.20 |
| Tyloxapol | 0.025 |
| Glycerin | 2.0 |
| Sodium Chloride | 0.03 |
| Sodium Hydroxide | qs, pH 7.2-7.4 |
| Purified Water | qs. 100 |

A batch of the above formulation was prepared by the following method:

Part 1 consisted of cyclosporin A dissolved in PEG 300 at ambient room temperature.

Part 2 consisted of the remaining ingredients prepared by dispersing carbomer in water, followed by the addition of the rest of the ingredients and pH adjustment with sodium hydroxide to the desired pH.

A stator-rotor OMNI mixer was introduced in Part 2, and, while mixing; Part 1 was added slowly to completion. A stable colloidal dispersion was obtained and submitted for particle size analysis using Horiba LA950 laser light scattering instrument. The mean particle size obtained was 180 nanometers. After 13.5 months storage at 2-8° C. of an unautoclaved sample, the mean particle size was 1.35 microns.

A sample of the batch was autoclaved at 121° C. for 30 minutes. The mean particle size for this sample was 2.322 microns. This suggested that the particle size was a function of the processing temperature selected. After 13.5 months storage at ambient room temperature the mean particle size of this sample was 2.377 microns. The stability of particle size in the autoclaved sample was remarkable, and may have been due to an annealing and stabilizing effect of temperature. In contrast, the increase in particle size in the unautoclaved sample may have been due to the higher solubility of cyclosporin A at lower temperatures leading to some Ostwald ripening.

Example 2

| Ingredient | % w/v |
| --- | --- |
| Cyclosporin A | 0.10 |
| Polyethylene Glycol 300 | 2.0 |
| Carbomer Homopolymer Type B | 0.06 |
| Tyloxapol | 0.025 |
| Glycerin | 2.0 |
| Sodium Hydroxide | qs, pH 7.2-7.4 |
| Purified Water | qs. 100 |

The batch was prepared as in Example 1. The mean particle size measured was 138 nanometers.

Example 3

In this example, a high concentration (0.5%) of cyclosporin A was used. The formulation did not require glycerin as tonicity adjuster because PEG 300 at 8% served as a solvent for cyclosporin A and tonicity adjuster for the final formulation.

| Ingredient | % w/v |
| --- | --- |
| Cyclosporin A | 0.50 |
| Polyethylene Glycol 300 | 8.0 |
| Carbomer Homopolymer Type B | 0.07 |
| Polysorbate 80 | 0.10 |
| Sodium Hydroxide | qs, pH 7.2-7.4 |
| Purified Water | qs. 100 |

The batch was prepared as in Example 1. The mean particle size measured was 183 nanometers.

Example 4

In this example, the formulation was designed to show that while it may be preferred to have a surfactant in the formulation to prevent aggregation of the primary particles, a colloidal dispersion could be obtained without it.

| Ingredient | % w/v |
| --- | --- |
| Cyclosporin A | 0.10 |
| Polyethylene Glycol 300 | 2.0 |
| Carbomer Homopolymer Type B | 0.07 |
| Mannitol | 4.0 |
| Sodium Hydroxide | qs, pH 7.2-7.4 |
| Purified Water | qs. 100 |

The batch was prepared as in Example 1. The mean particle size measured as function of sonication time in the instrument was as follows:

| Sonication Time | Particle Size |
| --- | --- |
| 90 seconds | 409 nanometers |
| 150 seconds | 279 nanometers |
| 210 seconds | 234 nanometers |

Example 5

In this example, a low concentration of alcohol, USP was used as a solvent for cyclosporin A.

| Ingredient | % w/v |
| --- | --- |
| Cyclosporin A | 0.05 |
| Alcohol | 1.0 |
| Carbomer Homopolymer Type B | 0.07 |
| Tyloxapol | 0.025 |
| Glycerin | 0.72 |
| Sodium Hydroxide | qs, pH 7.2-7.4 |
| Purified Water | qs. 100 |

The batch was prepared as in Example 1. The mean particle size measured was 2.19 microns.

Example 6

In this example, a carbomer copolymer (PEMULEN TR-2 polymer, manufactured by Lubrizol) is used instead of Carbomer Homopolymer Type B used in Example 1.

| Ingredient | % w/v |
| --- | --- |
| Cyclosporin A | 0.10 |
| Polyethylene Glycol 300 | 2.0 |
| Carbomer Copolymer Type A | 0.10 |
| Polysorbate 80 | 0.10 |
| Glycerin | 2.0 |
| Sodium Hydroxide | qs, pH 7.0-7.4 |
| Purified Water | qs. 100.00 |

Part 1 consisted of cyclosporin A dissolved in PEG 300 at ambient room temperature.
Part 2 consisted of the remaining ingredients prepared by dispersing carbomer coplymer in water, followed by the addition of the rest of the ingredients and pH adjustment with sodium hydroxide to the desired pH.

The batch was prepared as in Example 1. The mean particle size measured was 463 nanometers. The mean particle size after 8 months of storage at ambient room temperature was 1.144 microns.

Example 7

In this example, polyoxyl 15 hydroxystearate (SOLUTOL HS 15 polyoxyl 15 hydroxystearate, manufactured by BASF) is used both as a solvent for cyclosporin A at high temperature and as the surfactant/dispersing agent.

| Ingredient | % w/v |
| --- | --- |
| Cyclosporin A | 0.10 |
| Polyoxyl 15 Hydroxystearate | 0.50 |
| Carbomer Homopolymer Type B | 0.10 |
| Glycerin | 2.5 |
| Sodium Hydroxide | qs, pH 6.5-7.5 |
| Purified Water | qs. 100.00 |

Part 1 was prepared by melting SOLUTOL HS 15 polyoxyl 15 hydroxystearate and heating it to 60-70° C. Cyclosporin A was added and mixed until completely dissolved.
Part 2 consisted of the remaining ingredients (carbomer and glycerin) and was prepared by adding glycerin to water followed by dispersing carbomer in the solution and pH adjustment with sodium hydroxide to pH 6.55.

After heating Part 2 to 70-75° C. a stator-rotor OMNI mixer was introduced in the vessel, and, while mixing, Part 1 was added rapidly and mixed at high shear for about 10 minutes. At the end of mixing the temperature of the product was 53° C. The OMNI mixer was removed and replaced by a magnetic stir bar. The product was mixed to room temperature before sampling for particle size analysis using a Horiba LA950 laser light scattering instrument. The mean particle size obtained was 313 nanometers.

This example confirmed that substances that are solid at room temperature can be used as solvents for cyclosporin A when melted at higher temperatures.

Example 8

In this example, the stability of one of the disclosed formulations was assessed. Samples of the formulation described in Example 2 were stored continuously at 2-8° C., 25° C., or 40° C. and particle size was measured at various time points. The table below shows the particle size (mean particle size in nanometers) of the cyclosporin A particles in the formulation determined at initial time (time 0), 4 weeks, 18 weeks, and 39 weeks.

| | Mean Particle Size (nanometers) | | |
|---|---|---|---|
| | Temperature, ° C. | | |
| Time | 2-8 | 25 | 40 |
| Initial | 138 | 138 | 138 |
| 4 weeks | | | 235 |
| 18 weeks | 179 | 260 | 280 |
| 39 weeks | 264 | 740 | |

Example 9

In this example, the following samples (i.e., Samples 1-4) were tested by X-ray diffraction (XRD) to determine the crystallinity of the particles.

Sample 1: Cyclosporin A API used in all batches.

Sample 2: sample of the formulation described in Example 6 above. The sample was tested after about 6 months storage at ambient room temperature.

Sample 3: sample of the following formulation, which was about one month old at ambient room temperature:

| Ingredient | % w/v |
|---|---|
| Cyclosporin A | 0.10 |
| Tyloxapol | 0.025 |
| PEG300 | 2.0 |
| Glycerin | 2.0 |
| Benzalkonium Chloride | 0.010 |
| NaOH/HCl | adjust pH to 5-7 |
| Purified Water | q.s. 100.0 |

Sample 4: sample of the following formulation, which was about 8 months old at ambient room temperature:

| Ingredient | % w/v |
|---|---|
| Cyclosporin A | 0.10 |
| Hypromellose 2910 | 0.50 |

-continued

| Ingredient | % w/v |
|---|---|
| Polysorbate 80 | 0.050 |
| PEG300 | 2.0 |
| Glycerin | 2.0 |
| Benzalkonium Chloride | 0.010 |
| NaOH/HCl | adjust pH to 7-7.4 |
| Purified Water | q.s. 100.0 |

The results showed Sample 1 to match the known pattern of cyclosporin A Form 1. The solids filtered from Samples 2, 3, and 4 were amorphous. The dispersed particles appeared to maintain their amorphous nature after prolonged storage and not just immediately after preparation.

Example 10

This example was a pharmacokinetics study conducted to compare ocular distribution of a 0.05% cyclosporin A suspension according to the present disclosure to RESTASIS® (cyclosporin A ophthalmic emulsion, 0.05%) in New Zealand white rabbits. The cyclosporin A suspension formulation used in the study was as follows:

| Ingredient | % w/v |
|---|---|
| Cyclosporin A | 0.05 |
| Polyethylene Glycol 300 | 1.0 |
| Carbomer Homopolymer Type B | 0.08 |
| Carbomer Copolymer Type A | 0.02 |
| Polysorbate 80 | 0.05 |
| Glycerin | 2.3 |
| Sodium Hydroxide | qs, pH 7.0-7.4 |
| Purified Water | qs. 100.00 |

The study design was as set forth in the table below.

| Study Design and Group Assignment | | | | | |
|---|---|---|---|---|---|
| Group | Dose Route (OU*) | Test Article | Dose Volume (μL per eye) | Termination Time Points | Matrices Collected |
| 1 (n = 8 animals) | Ocular, Topical | Restasis cyclosporin A emulsion (0.05%) | 50[a] | 2 hours (n = 2) 4 hours (n = 2) 8 hours (n = 2) and 24 hours (n = 2) | Tears, cornea, conjunctiva |
| 2 (n = 8 animals) | Ocular, Topical | Cyclosporin A suspension (0.05%) | 50 | 2 hours (n = 2) 4 hours (n = 2) 8 hours (n = 2) and 24 hours (n = 2) | Tears, cornea, conjunctiva |
| 3 (n = 2 animals) | Ocular, Topical | Placebo (Vehicle Control) | 50 | NA | NA |

*OU: both eyes; [a]The supplied commercial dose units of Restasis were pooled so that equivalent doses of 50 μL were applied to all animals.

The groups were assigned as set forth above. Animals were subjected to pre-treatment examinations and In-Life observations and measurements. These included: routine general health/gross ocular observations, and clinical ophthalmic observations. Animals were dosed with 50 μL of the test article as set forth above. Two animals were sacrificed at each timepoint for groups 1 and 2 and the indicated matrices were collected for analysis of cyclosporin A level. No tissues were collected from Group 3 animals. Ocular exams occurred 24 hours post-dose for all Group 3 animals.

Figure 2:
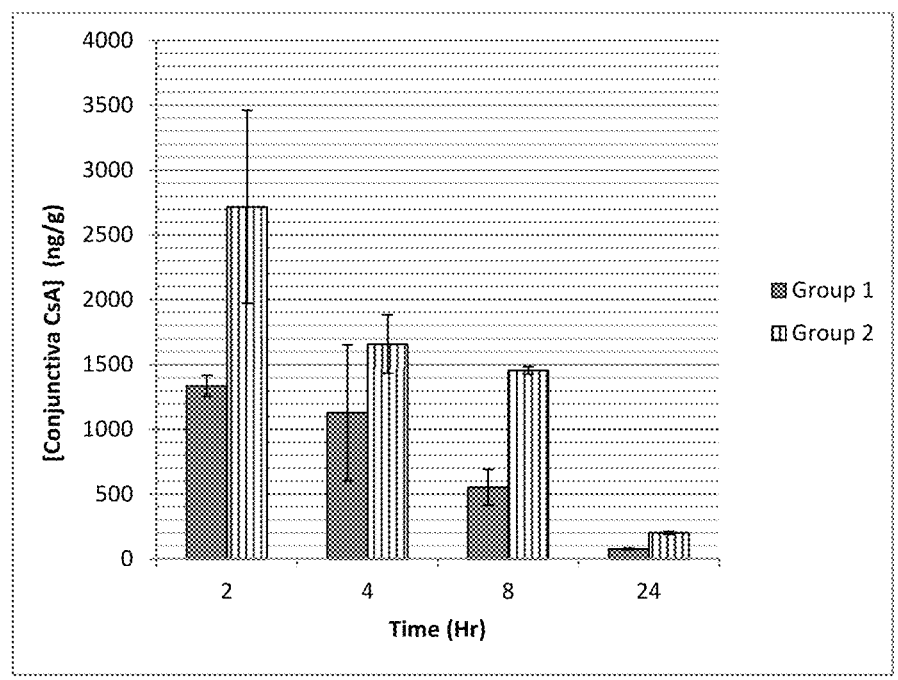
FIG. 2 is a plot of the cyclosporin A levels in conjunctiva tissues from rabbits at the indicated time points in a study comparing a 0.05% cyclosporin A emulsion (Group 1) to a 0.05% cyclosporin A suspension of the present disclosure (Group 2).

The concentration of cyclosporin A was measured in tissue from the cornea and conjunctiva of the OD eye of each animal Groups 1 and 2 for each time point. The results are shown in FIG. 1 (cornea) and FIG. 2 (conjunctiva). The calibration was against a standard curve generated in MeOH. The error bars are the range of the two data points from the OD eyes. These data indicate that there is a significant difference between Group 1 and Group 2, that is, tissue levels of cyclosporin A were higher in animals dosed with the cyclosporin A suspension than in animals dosed with the cyclosporin A emulsion.

Examples 11-40 below are prepared in accordance with the procedure of this paragraph which is based on the concept of mixing a solvent part to an antisolvent part of the composition to yield nano/micro suspensions of cyclosporin in an ophthalmic formulation. For example, Part 1 includes cyclosporin plus a solvent or mixture of solvents such as polyethylene glycol, propylene glycol, benzyl alcohol, etc. Part 2 (the antisolvent) contains the rest of the ingredients in the formulation. Mixing parameters such as speed of mixing, shear, temperature, etc. are optimized for each composition to yield the desired properties.

Example 11

| Ingredient | % w/v |
|---|---|
| Cyclosporin | 0.030 |
| Polyethylene Glycol 300 | 1.0 |
| Sodium Hyaluronate | 0.30 |
| Tyloxapol | 0.020 |
| Glycerin | 2.20 |
| Sodium Hydroxide/Hydrochloric Acid | q.s. pH 6.5-7.5 |
| Purified Water/Water for Injection | q.s. 100 |

Example 12

| Ingredient | % w/v |
|---|---|
| Cyclosporin | 0.050 |
| Polyethylene Glycol 300 | 1.0 |
| Benzyl Alcohol | 0.050 |
| Carbomer Homopolymer Type B | 0.060 |
| Tyloxapol | 0.0250 |
| Sorbitol | 4.7 |
| Sodium Hydroxide | q.s. pH 7-7.4 |
| Purified Water/Water for Injection | q.s. 100 |

Example 13

| Ingredient | % w/v |
|---|---|
| Cyclosporin | 0.10 |
| Polyethylene Glycol 300 | 2.0 |
| Carbomer Homopolymer Type B | 0.10 |
| Acacia | 0.10 |
| Tyloxapol | 0.030 |
| Poloxamer | 0.10 |
| Mannitol | 4.0 |
| Sodium Hydroxide | q.s. pH 6.8-7.4 |
| Purified Water/Water for Injection | q.s. 100 |

Example 14

| Ingredient | % w/v |
|---|---|
| Cyclosporin | 0.120 |
| Polyethylene Glycol 300 | 2.0 |
| Alcohol | 0.10 |
| Xanthan Gum | 0.50 |
| Povidone K-90 | 0.50 |
| Tyloxapol | 0.10 |
| Sodium Chloride | 0.65 |
| Sodium Hydroxide/Hydrochloric Acid | q.s. pH 6.5-7.5 |
| Purified Water/Water for Injection | q.s. 100 |

Example 15-1

| Ingredient | % w/v |
|---|---|
| Cyclosporin | 0.20 |
| Propylene Glycol | 0.60 |
| Polyethylene Glycol 3350 | 0.50 |
| Hypromellose | 0.50 |
| Tyloxapol | 0.10 |
| Poloxamer | 0.50 |
| Sodium Chloride | 0.60 |
| Edetate Disodium | 0.010 |
| Benzalkonium Chloride | 0.010 |
| Sodium Hydroxide/Hydrochloric Acid | q.s. pH 6.5-7.5 |
| Purified Water/Water for Injection | q.s. 100 |

Example 15-2

| Ingredient | % w/v |
|---|---|
| Cyclosporin | 0.10 |
| Benzyl Alcohol | 0.10 |
| Xanthan Gum | 0.40 |
| Tyloxapol | 0.025 |
| Glycerin | 2.20 |
| Sodium Hydroxide/Hydrochloric Acid | q.s. pH 6.5-7.5 |
| Purified Water/Water for Injection | q.s. 100 |

Example 16

| Ingredient | % w/v |
|---|---|
| Cyclosporin | 0.010 |
| Polyethylene Glycol 300 | 2.0 |
| Tyloxapol | 0.020 |
| Glycerin | 2.0 |
| Carbomer Homopolymer Type 13 | 0.070 |
| Sodium Hydroxide/Hydrochloric Acid | q.s. pH 6.5-7.5 |
| Purified Water/Water for Injection | q.s. 100 |

Example 17

| Ingredient | % w/v |
|---|---|
| Cyclosporin | 0.010 |
| Polyethylene Glycol 300 | 1.0 |

Example 18

| Ingredient | % w/v |
| --- | --- |
| Cyclosporin | 0.010 |
| Polyethylene Glycol 300 | 1.0 |
| Tyloxapol | 0.020 |
| Alcohol | 1.0 |
| Hypromellose | 0.50 |
| Sodium Hydroxide/Hydrochloric Acid | q.s. pH 6.5-7.5 |
| Purified Water/Water for Injection | q.s. 100 |

Example 19

| Ingredient | % w/v |
| --- | --- |
| Cyclosporin | 0.010 |
| Polyethylene Glycol 300 | 1.0 |
| Carbomer Homopolymer Type B | 0.10 |
| Poloxamer | 0.10 |
| Sodium Hydroxide/Hydrochloric Acid | q.s. pH 6.8-7.4 |
| Purified Water/Water for Injection | q.s. 100 |

Example 20

| Ingredient | % w/v |
| --- | --- |
| Cyclosporin | 0.030 |
| Polyethylene Glycol 300 | 2.0 |
| Tyloxapol | 0.020 |
| Acacia | 0.10 |
| Sodium Hydroxide/Hydrochloric Acid | q.s. pH 6.5-7.5 |
| Purified Water/Water for Injection | q.s. 100 |

Example 21

| Ingredient | % w/v |
| --- | --- |
| Cyclosporin | 0.030 |
| Glycerin | 1.0 |
| Sorbitol | 3.0 |
| Poloxamer | 0.30 |
| Polyethylene glycol 3350 | 0.60 |
| Sodium Hydroxide/Hydrochloric Acid | q.s. pH 6.8-7.4 |
| Purified Water/Water for Injection | q.s. 100 |

-continued

| Ingredient | % w/v |
| --- | --- |
| Sodium Hyaluronate | 0.10 |
| Tyloxapol | 0.010 |
| Glycerin | 1.0 |
| Sodium Hydroxide/Hydrochloric Acid | q.s. pH 6.8-7.5 |
| Purified Water/Water for Injection | q.s. 100 |

Example 22

| Ingredient | % w/v |
| --- | --- |
| Cyclosporin | 0.030 |
| Polyethylene Glycol 300 | 1.0 |
| Tyloxapol | 0.030 |
| Benzyl alcohol | 0.050 |
| Carbomer Homopolymer Type B | 0.050 |
| Sodium Hydroxide/Hydrochloric Acid | q.s. pH 6.8-7.4 |
| Purified Water/Water for Injection | q.s. 100 |

Example 23

| Ingredient | % w/v |
| --- | --- |
| Cyclosporin | 0.030 |
| Sodium hyaluronate | 0.30 |
| Tyloxapol | 0.0250 |
| Alcohol | 1.0 |
| Xanthan gum | 0.50 |
| Propylene glycol | 0.60 |
| Sodium Hydroxide/Hydrochloric Acid | q.s. pH 6.5-7.5 |
| Purified Water/Water for Injection | q.s. 100 |

Example 24

| Ingredient | % w/v |
| --- | --- |
| Cyclosporin | 0.050 |
| Polyethylene Glycol 300 | 1.0 |
| Sodium Hyaluronate | 0.20 |
| Poloxamer | 0.10 |
| Povidone K-90 | 0.50 |
| Sodium Chloride | 0.50 |
| Hypromellose | 0.50 |
| Sodium Hydroxide/Hydrochloric Acid | q.s. pH 7-7.4 |
| Purified Water/Water for Injection | q.s. 100 |

Example 25

| Ingredient | % w/v |
| --- | --- |
| Cyclosporin | 0.050 |
| Polyethylene Glycol 300 | 1.0 |
| Tyloxapol | 0.030 |
| Acacia | 0.10 |
| Edetate disodium | 0.010 |
| Sodium Hydroxide/Hydrochloric Acid | q.s. pH 6.5-7.5 |
| Purified Water/Water for Injection | q.s. 100 |

Example 26

| Ingredient | % w/v |
| --- | --- |
| Cyclosporin | 0.050 |
| Polyethylene Glycol 300 | 1.0 |
| Tyloxapol | 0.020 |
| Carbomer Homopolymer Type B | 0.050 |
| Xanthan Gum | 0.10 |

Example 27

| Ingredient | % w/v |
|---|---|
| Cyclosporin | 0.030 |
| Benzyl alcohol | 0.050 |
| Sorbitol | 1.0 |
| Poloxamer | 0.150 |
| Alcohol | 1.0 |
| Propylene glycol | 0.50 |
| Polyethylene glycol 3350 | 0.50 |
| Benzalkonium Chloride | 0.01 |
| Sodium Hydroxide/Hydrochloric Acid | q.s. pH 6.5-7.5 |
| Purified Water/Water for Injection | q.s. 100 |

Example 28

| Ingredient | % w/v |
|---|---|
| Cyclosporin | 0.0750 |
| Polyethylene Glycol 300 | 2.0 |
| Sodium Hyaluronate | 0.50 |
| Tyloxapol | 0.030 |
| Mannitol | 2.0 |
| Sodium Hydroxide/Hydrochloric Acid | q.s. pH 6.8-7.4 |
| Purified Water/Water for Injection | q.s. 100 |

Example 29

| Ingredient | % w/v |
|---|---|
| Cyclosporin | 0.0750 |
| Polyethylene Glycol 300 | 1.0 |
| Tyloxapol | 0.0250 |
| Carbomer Homopolymer Type B | 0.080 |
| Edetate Disodium | 0.010 |
| Sodium Hydroxide/Hydrochloric Acid | q.s. pH 6.5-7.5 |
| Purified Water/Water for Injection | q.s. 100 |

Example 30

| Ingredient | % w/v |
|---|---|
| Cyclosporin | 0.0750 |
| Polyethylene Glycol 300 | 1.0 |
| Tyloxapol | 0.050 |
| Xanthan Gum | 0.30 |
| Povidone K-90 | 0.30 |
| Sodium Chloride | 0.40 |
| Sodium Hydroxide/Hydrochloric Acid | q.s. pH 7-7.5 |
| Purified Water/Water for Injection | q.s. 100 |

-continued

| Ingredient | % w/v |
|---|---|
| Sodium Hydroxide/Hydrochloric Acid | q.s. pH 6.8-7.4 |
| Purified Water/Water for Injection | q.s. 100 |

Example 31

| Ingredient | % w/v |
|---|---|
| Cyclosporin | 0.0750 |
| Glycerin | 2.0 |
| Acacia | 0.10 |
| Poloxamer | 0.10 |
| Alcohol | 0.50 |
| Hypromellose | 0.60 |
| Sodium Hydroxide/Hydrochloric Acid | q.s. pH 6.8-7.4 |
| Purified Water/Water for Injection | q.s. 100 |

Example 32

| Ingredient | % w/v |
|---|---|
| Cyclosporin | 0.10 |
| Polyethylene Glycol 300 | 2.0 |
| Tyloxapol | 0.050 |
| Glycerin | 2.0 |
| Carbomer Homopolymer Type 13 | 0.10 |
| Sodium Hydroxide/Hydrochloric Acid | q.s. pH 6.5-7 |
| Purified Water/Water for Injection | q.s. 100 |

Example 33

| Ingredient | % w/v |
|---|---|
| Cyclosporin | 0.10 |
| Polyethylene Glycol 300 | 2.0 |
| Sodium Hyaluronate | 0.50 |
| Poloxamer | 0.20 |
| Xanthan Gum | 0.10 |
| Sodium Hydroxide/Hydrochloric Acid | q.s. pH 7-7.4 |
| Purified Water/Water for Injection | q.s. 100 |

Example 34

| Ingredient | % w/v |
|---|---|
| Cyclosporin | 0.10 |
| Tyloxapol | 0.0250 |
| Glycerin | 2.0 |
| Acacia | 0.10 |
| Sodium Chloride | 0.030 |
| Propylene Glycol | 0.50 |
| Polyethylene Glycol 3350 | 0.50 |
| Sodium Hydroxide/Hydrochloric Acid | q.s. pH 6.8-7.4 |
| Purified Water/Water for Injection | q.s. 100 |

Example 35

| Ingredient | % w/v |
|---|---|
| Cyclosporin | 0.150 |
| Polyethylene Glycol 300 | 2.0 |
| Tyloxapol | 0.10 |
| Sodium Chloride | 0.60 |
| Propylene Glycol | 0.60 |

-continued

| Ingredient | % w/v |
| --- | --- |
| Polyethylene Glycol 3350 | 0.50 |
| Hypromellose | 0.50 |
| Edetate Disodium | 0.010 |
| Benzalkonium Chloride | 0.010 |
| Sodium Hydroxide/Hydrochloric Acid | q.s. pH 6.5-7.5 |
| Purified Water/Water for Injection | q.s. 100 |

Example 36

| Ingredient | % w/v |
| --- | --- |
| Cyclosporin | 0.150 |
| Polyethylene Glycol 300 | 2.0 |
| Sodium Hyaluronate | 0.30 |
| Tyloxapol | 0.10 |
| Mannitol | 2.0 |
| Alcohol | 1.0 |
| Sodium Hydroxide/Hydrochloric Acid | q.s. pH 6.5-7 |
| Purified Water/Water for Injection | q.s. 100 |

Example 37

| Ingredient | % w/v |
| --- | --- |
| Cyclosporin | 0.150 |
| Glycerin | 1.0 |
| Benzyl Alcohol | 1.0 |
| Carbomer Homopolymer Type B | 0.150 |
| Poloxamer | 0.50 |
| Xanthan Gum | 0.50 |
| Povidone K-90 | 0.50 |
| Sodium Hydroxide/Hydrochloric Acid | q.s. pH 6.8-7.4 |
| Purified Water/Water for Injection | q.s. 100 |

Example 38

| Ingredient | % w/v |
| --- | --- |
| Cyclosporin | 0.20 |
| Polyethylene Glycol 300 | 2.0 |
| Sodium Hyaluronate | 0.30 |
| Tyloxapol | 0.10 |
| Glycerin | 0.50 |
| Alcohol | 0.050 |
| Sodium Chloride | 0.20 |
| Sodium Hydroxide/Hydrochloric Acid | q.s. pH 6.5-7.5 |
| Purified Water/Water for Injection | q.s. 100 |

Example 39

| Ingredient | % w/v |
| --- | --- |
| Cyclosporin | 0.20 |
| Polyethylene Glycol 300 | 2.0 |
| Tyloxapol | 0.10 |
| Benzyl Alcohol | 0.050 |
| Carbomer Homopolymer Type B | 0.20 |
| Xanthan Gum | 0.50 |

-continued

| Ingredient | % w/v |
| --- | --- |
| Povidone K-90 | 0.50 |
| Sodium Hydroxide/Hydrochloric Acid | q.s. pH 6.7-7.3 |
| Purified Water/Water for Injection | q.s. 100 |

Example 40

| Ingredient | % w/v |
| --- | --- |
| Cyclosporin | 0.20 |
| Glycerin | 2.0 |
| Poloxamer | 0.50 |
| Mannitol | 2.0 |
| Hypromellose | 0.50 |
| Edetate Disodium | 0.010 |
| Benzalkonium Chloride | 0.010 |
| Sodium Hydroxide/Hydrochloric Acid | q.s. pH 6.5-7.5 |
| Purified Water/Water for Injection | q.s. 100 |

Although the present disclosure has been described with reference to the above examples, it will be understood that modifications and variations are encompassed within the spirit and scope of the disclosure.

The following embodiments are specifically contemplated.

Embodiment 1. A pharmaceutical composition comprising: cyclosporin A, a formulation aid, water, and 1) a dispersing agent or a 2) suspending agent.

Embodiment 2. The pharmaceutical composition of Embodiment 1 or Embodiment 2, wherein the cyclosporin is cyclosporin A.

Embodiment 3. The method of embodiment 2, wherein the pharmaceutical composition contains about 0.01% w/v to about 0.05% w/v of the cyclosporin A.

Embodiment 4. The method of embodiment 2, wherein the pharmaceutical composition contains about 0.05% w/v to about 0.1% w/v of the cyclosporin A.

Embodiment 5. The method of embodiment 2, wherein the pharmaceutical composition contains about 0.1% w/v to about 0.5% w/v of the cyclosporin A.

Embodiment 6. The method of embodiment 2, wherein the pharmaceutical composition contains about 0.5% w/v to about 1% w/v of the cyclosporin A.

Embodiment 7. The method of embodiment 1, 2, 3, 4, 5, or 6, wherein the pharmaceutical composition contains about 0.01% w/v to about 1% w/v of the formulation aid.

Embodiment 8. The method of embodiment 1, 2, 3, 4, 5, or 6, wherein the pharmaceutical composition contains about 1% w/v to about 5% w/v of the formulation aid.

Embodiment 9. The method of embodiment 1, 2, 3, 4, 5, or 6, wherein the pharmaceutical composition contains about 5% w/v to about 10% w/v of the formulation aid.

Embodiment 10. The method of embodiment 1, 2, 3, 4, 5, 6, 7, 8, or 9, wherein the pharmaceutical composition contains about 0.005% w/v to about 1% w/v of the dispersing agent.

Embodiment 11. The method of embodiment 1, 2, 3, 4, 5, 6, 7, 8, or 9, wherein the pharmaceutical composition contains about 1% w/v to about 2% w/v of the dispersing agent.

Embodiment 12. The method of embodiment 1, 2, 3, 4, 5, 6, 7, 8, or 9, wherein the pharmaceutical composition contains about 2% w/v to about 3% w/v of the dispersing agent.

Embodiment 13. The method of embodiment 1, 2, 3, 4, 5, 6, 7, 8, or 9, wherein the pharmaceutical composition contains about 3% w/v to about 4% w/v of the dispersing agent.

Embodiment 14. The method of embodiment 1, 2, 3, 4, 5, 6, 7, 8, or 9, wherein the pharmaceutical composition contains about 4% w/v to about 5% w/v of the dispersing agent.

Embodiment 15. The method of embodiment 1, 2, 3, 4, 5, 6, 7, 8, or 9, wherein the pharmaceutical composition contains about 0.005% w/v to about 1% w/v of the dispersing agent.

Embodiment 16. The method of embodiment 1, 2, 3, 4, 5, 6, 7, 8, 9, 10, 11, 12, 13, 14, or 15, wherein the pharmaceutical composition contains about 1% w/v to about 2% w/v of the suspending agent.

Embodiment 17. The method of embodiment 1, 2, 3, 4, 5, 6, 7, 8, 9, 10, 11, 12, 13, 14, or 15, wherein the pharmaceutical composition contains about 2% w/v to about 3% w/v of the suspending agent.

Embodiment 18. The method of embodiment 1, 2, 3, 4, 5, 6, 7, 8, 9, 10, 11, 12, 13, 14, or 15, wherein the pharmaceutical composition contains about 3% w/v to about 4% w/v of the suspending agent.

Embodiment 19. The method of embodiment 1, 2, 3, 4, 5, 6, 7, 8, 9, 10, 11, 12, 13, 14, or 15, wherein the pharmaceutical composition contains about 4% w/v to about 5% w/v of the suspending agent.

Embodiment 20. A method of treating an ophthalmic disorder, comprising administering a composition of embodiment 1, 2, 3, 4, 5, 6, 7, 8, 9, 10, 11, 12, 13, 14, 15, 16, 17, 18, or 19 to a mammal in need thereof, wherein a therapeutic effect is observed after administering the pharmaceutical composition.

Embodiment 21. The method of embodiment 20, wherein the mammal is a human being.

Embodiment 22. Use of a composition embodiment 1, 2, 3, 4, 5, 6, 7, 8, 9, 10, 11, 12, 13, 14, 15, 16, 17, 18, or 19 in the manufacture of a medicament for the treatment of an ophthalmic disorder.

Embodiment 23. The method of embodiment 20 or 21, or the use of embodiment 22, wherein the disorder is dry eye syndrome.

Embodiment 24. The method of embodiment 20 or 21, or the use of embodiment 22, wherein the disorder is anterior uveitis.

Embodiment 25. The method of embodiment 20 or 21, or the use of embodiment 22, wherein the disorder is posterior uveitis.

Embodiment 26. The method of embodiment 20 or 21, or the use of embodiment 22, wherein the disorder is chronic keratitis.

Embodiment 27. The method of embodiment 20 or 21, or the use of embodiment 22, wherein the disorder is keratoconjunctivitis sicca.

Embodiment 28. The method of embodiment 20 or 21, or the use of embodiment 22, wherein the disorder is vernal keratoconjunctivitis.

Embodiment 29. The method of embodiment 20 or 21, or the use of embodiment 22, wherein the disorder is phacoanaphylactic endophthalmitis.

Embodiment 30. The method of embodiment 20 or 21, or the use of embodiment 22, wherein the disorder is atopic keratoconjunctivitis.

Embodiment 31. The method of embodiment 20 or 21, or the use of embodiment 22, wherein the disorder is conjunctivitis.

Embodiment 32. The method of embodiment 20 or 21, or the use of embodiment 22, wherein the disorder is vernal conjunctivitis.

Embodiment 33. The method of embodiment 20 or 21, or the use of embodiment 22, wherein the disorder is keratoplasty.

Embodiment 34. The method of embodiment 20 or 21, or the use of embodiment 22, wherein the disorder is immunoreactive graft rejection post corneal transplantation.

Embodiment 35. The method of embodiment 20 or 21, or the use of embodiment 22, wherein the disorder is Behcet disease.

Embodiment 36. The method of embodiment 20 or 21, or the use of embodiment 22, wherein the disorder is Mooren's ulcer.

Embodiment 37. The method of embodiment 20 or 21, or the use of embodiment 22, wherein the disorder is ocular pemphigus.

Embodiment 38. The method of embodiment 20 or 21, or the use of embodiment 22, wherein the disorder is rheumatoid ulcer.

What is claimed is:

1. A method of producing a suspension of cyclosporin A comprising mixing a cyclosporin A solution into an aqueous mixture to precipitate cyclosporin A particles having a particle size of 20 µm or less as determined by laser light scattering;
    wherein the cyclosporin A solution comprises cyclosporin A that is completely dissolved in polyethylene glycol prior to being mixed with the aqueous mixture;
    wherein the aqueous mixture comprises a polysorbate, carbomer homopolymer, a carbomer copolymer, a carbomer interpolymer, a salt thereof, or a combination thereof, and an aqueous vehicle;
    wherein the suspension of cyclosporin A comprises about 0.01% (w/v) to about 0.1 (w/v) % of cyclosporin A in the form of solid particles having a particle size of 20 µm or less as determined by laser light scattering; about 0.1% (w/v) to about 2.5% (w/v) of polyethylene glycol; about 0.01% (w/v) to about 0.5% (w/v) of the carbomer homopolymer, the carbomer copolymer, the carbomer interpolymer, the salt thereof, or the combination thereof; about 0.5% (w/v) or less of the polysorbate, about 0.1% (w/v) to about 5% (w/v) of glycerin, and water, and wherein the suspension of cyclosporin A is oil-free and fat free.

2. The method of claim 1, wherein the suspension of cyclosporin A comprises cyclosporin A particles of 5 µm or less.

3. The method of claim 1, wherein the cyclosporin A particles are amorphous.

4. The method of claim 1, wherein the suspension of cyclosporin A comprises about 0.05% (w/v) to about 0.1 (w/v) % of cyclosporin A and about 2% (w/v) to about 2.5% (w/v) of glycerin.

5. A method of producing a suspension of cyclosporin A comprising mixing a cyclosporin A solution into an aqueous mixture to precipitate cyclosporin A particles having a particle size of 20 µm or less as determined by laser light scattering, wherein the weight ratio of the aqueous mixture to the cyclosporin A solution is about 27:1 to about 951:1;
    wherein the cyclosporin A solution comprises cyclosporin A that is completely dissolved in a hydrophilic solvent prior to being mixed with the aqueous mixture;
    wherein the aqueous mixture comprises a surfactant, a suspending agent, and an aqueous vehicle;
    wherein the suspension of cyclosporin A comprise about 0.005% (w/v) to about 1 (w/v) % of cyclosporin A in the form of solid particles having a particle size of 20 µm or less as determined by laser light scattering; about 0.1% (w/v) to about 2.5% (w/v) of the hydrophilic solvent, about 0.5% (w/v) or less of the surfactant, and about 0.01% (w/v) to about 0.5% (w/v) of the suspending agent, and wherein the suspension of cyclosporin A is oil-free and fat free.

6. The method of claim 5, wherein the hydrophilic solvent comprises ethanol.

7. The method of claim 5, wherein the hydrophilic solvent comprises propylene glycol.

8. The method of claim 5, wherein the hydrophilic solvent comprises polyethylene glycol.

9. The method of claim 5, wherein the hydrophilic solvent comprises glycerin.

10. The method of claim 5, wherein the hydrophilic solvent comprises benzyl alcohol.

11. The method of claim 5, wherein the hydrophilic solvent comprises a polysorbate.

12. The method of claim 5, wherein the hydrophilic solvent comprises tyloxapol.

13. The method of claim 5, wherein the hydrophilic solvent comprises a poloxamer.

14. The method of claim 5, wherein the hydrophilic solvent comprises acetone.

15. The method of claim 5, wherein the hydrophilic solvent comprises DMSO.

16. The method of claim 5, wherein the hydrophilic solvent comprises polyoxyl 15 hydroxystearate.

17. The method of claim 5, wherein the hydrophilic solvent comprises a hydrophilic surfactant that is solid at room temperature and acts as a solvent when melted.

18. The method of claim 5, wherein the dispersing agent is a surfactant.

19. The method of claim 5, wherein the surfactant is polysorbate 80, polysorbate 60, polysorbate 40, polysorbate 20, polyoxyl 40 stearate, polyoxyl 15 hydroxystearate, poloxamers, tyloxapol, POE 35 castor oil, or a combination thereof.

20. The method of claim 5, wherein the surfactant is a hydrophilic surfactant.

21. The method of claim 5, wherein the suspending agent is an acrylic acid homopolymer, an acrylic acid copolymer, an acrylic acid interpolymer, polycarbophil, a soluble cellulose derivative, polyvinyl alcohol, polyvinylpyrrolidone, hyaluronic acid, chondroitin sulfate, gellan, a natural natural gum, a salt thereof, or a combination thereof.

* * * * *

UNITED STATES PATENT AND TRADEMARK OFFICE
CERTIFICATE OF CORRECTION

PATENT NO. : 11,090,356 B2
APPLICATION NO. : 17/153736
DATED : August 17, 2021
INVENTOR(S) : Harun Takruri It is certified that error appears in the above-identified patent and that said Letters Patent is hereby corrected as shown below:

On the Title Page

Delete Title Page and Replace with attached Title Page.

In the Claims

In Column 94, Lines 26-27: Claim 1, Replace "wherein the aqueous mixture comprises a polysorbate carbomer homopolymer, a carbomer copolymer, a carbomer..." with -- wherein the aqueous mixture comprises a polysorbate, carbomer homopolymer, a carbomer copolymer, a carbomer --.

In Column 96, Lines 6-7: Remove Claim 18.

In Column 96, Line 8: delete "19" and replace with -- 18 --.

In Column 96, Line 13: delete "20" and replace with -- 19 --.

In Column 96, Line 15: delete "21" and replace with -- 20 --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

(12) United States Patent
Takruri

(10) Patent No.: US 11,090,356 B2
(45) Date of Patent: *Aug. 17, 2021

(54) AQUEOUS SUSPENSIONS OF CYCLOSPORIN

(71) Applicant: NEWPORT RESEARCH, INC., Newport Beach, CA (US)

(72) Inventor: Harun Takruri, Newport Beach, CA (US)

(73) Assignee: NEWPORT RESEARCH, INC., Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/153,736

(22) Filed: Jan. 20, 2021

(65) Prior Publication Data
US 2021/0138027 A1 May 13, 2021

Related U.S. Application Data

(63) Continuation of application No. 16/750,694, filed on Jan. 23, 2020, and a continuation-in-part of application No. 14/597,948, filed on Jan. 15, 2015, now abandoned.

(60) Provisional application No. 62/797,584, filed on Jan. 28, 2019, provisional application No. 62/797,080, filed on Jan. 25, 2019.

(51) Int. Cl.
*A61K 38/13* (2006.01)
*A61K 47/10* (2017.01)
*A61K 47/36* (2006.01)
*A61K 47/38* (2006.01)
*A61K 47/12* (2006.01)
*A61K 47/26* (2006.01)
*A61K 47/02* (2006.01)
*A61K 47/18* (2017.01)
*A61K 47/32* (2006.01)

(52) U.S. Cl.
CPC ............ *A61K 38/13* (2013.01); *A61K 47/02* (2013.01); *A61K 47/10* (2013.01); *A61K 47/12* (2013.01); *A61K 47/186* (2013.01); *A61K 47/26* (2013.01); *A61K 47/32* (2013.01); *A61K 47/36* (2013.01); *A61K 47/38* (2013.01)

(58) Field of Classification Search
CPC ........ A61K 38/13; A61K 47/10; A61K 47/36; A61K 47/38; A61K 47/12; A61K 47/26; A61K 47/02; A61K 47/186; A61K 47/32; A61K 9/08; A61K 9/0019; A61K 9/0048
See application file for complete search history.

(56) References Cited

U.S. PATENT DOCUMENTS

| | | | |
|---|---|---|---|
| 5,474,979 A | 12/1995 | Ding et al. | |
| 5,827,822 A | 10/1998 | Floc'h et al. | |
| 6,008,192 A * | 12/1999 | Al-Razzak | A61P 31/12 514/20.5 |
| 6,465,016 B2 | 10/2002 | Parikh et al. | |
| 6,656,460 B2 | 12/2003 | Benita et al. | |
| 7,026,290 B1 | 4/2006 | Domb | |
| 7,335,682 B2 | 2/2008 | Chen et al. | |
| 8,298,569 B2 | 10/2012 | Philips et al. | |
| 8,414,904 B2 | 4/2013 | Carli et al. | |
| 8,685,930 B2 | 4/2014 | Acheampong et al. | |
| 8,969,385 B2 | 3/2015 | Aberg et al. | |
| 9,974,793 B2 | 5/2018 | Ottoboni et al. | |
| 10,137,083 B2 | 11/2018 | Lee et al. | |
| 10,154,959 B1 | 12/2018 | Steele | |
| 10,154,994 B2 | 12/2018 | Nguyen et al. | |
| 10,918,694 B2 | 2/2021 | Weiss et al. | |
| 2002/0013271 A1 | 1/2002 | Parikh et al. | |
| 2003/0185892 A1 | 10/2003 | Bell et al. | |
| 2004/0115287 A1 | 6/2004 | Chen et al. | |
| 2004/0267214 A1 | 12/2004 | Kerssies | |
| 2005/0059583 A1 | 3/2005 | Acheampong et al. | |
| 2006/0148686 A1 | 7/2006 | Xia et al. | |
| 2006/0210622 A1 | 9/2006 | Pace et al. | |
| 2008/0124389 A1 | 5/2008 | Jenkins et al. | |
| 2008/0161382 A1 | 7/2008 | Desai et al. | |
| 2008/0299206 A1 | 12/2008 | Lee et al. | |
| 2009/0074889 A1 | 3/2009 | Amador et al. | |
| 2012/0028910 A1 | 2/2012 | Combal et al. | |
| 2012/0225827 A1 | 9/2012 | Warner et al. | |
| 2013/0005665 A1 | 1/2013 | Gore et al. | |
| 2015/0202150 A1 | 7/2015 | Mitra et al. | |
| 2019/0076354 A1 | 3/2019 | Lee et al. | |

(Continued)

FOREIGN PATENT DOCUMENTS

| | | |
|---|---|---|
| AU | 2016283517 B2 | 1/2019 |
| AU | 2020203052 A1 | 5/2020 |

(Continued)

OTHER PUBLICATIONS

Tam et al (Journal of Pharmaceutical Sciences, vol. 97, No. 11, Nov. 2008) (Year: 2008).*

(Continued)

*Primary Examiner* — Sudhakar Katakam
(74) *Attorney, Agent, or Firm* — Maschoff Brennan; Brent A. Johnson

(57) ABSTRACT

Compositions that are aqueous suspensions of cyclosporin and contain a cyclosporin (e.g., cyclosporin A), a pharmaceutically acceptable water soluble solvent for the cyclosporin, a dispersing agent, a suspending agent and an aqueous vehicle are disclosed. Methods of producing such compositions, as well as methods of using the compositions to treat ophthalmic disorders are also disclosed.

20 Claims, 1 Drawing Sheet